United States Patent [19]
Bonutti et al.

[11] Patent Number: 6,113,562
[45] Date of Patent: Sep. 5, 2000

[54] SHOULDER ORTHOSIS

[75] Inventors: Peter M. Bonutti, 1303 W. Evergreen Plz., Effingham, Ill. 62401; Christopher A. Leo, Effingham; Kevin R. Ruholl, Teutopolis, both of Ill.

[73] Assignee: Peter M. Bonutti, Effingham, Ill.

[21] Appl. No.: 09/088,134

[22] Filed: Jun. 1, 1998

[51] Int. Cl.[7] .................................................. A61F 5/00
[52] U.S. Cl. ................................ 602/20; 602/5; 602/16; 602/21
[58] Field of Search .................................. 602/5, 16, 20, 602/23, 26, 27, 3, 36–38; 601/23, 33, 40, 5, 27, 32, 34; 128/898; 482/124, 130, 139, 44, 45, 46

[56] References Cited

U.S. PATENT DOCUMENTS

| | | |
|---|---|---|
| 4,180,870 | 1/1980 | Radulovic et al. . |
| 5,285,773 | 2/1994 | Bonutti et al. . |
| 5,391,132 | 2/1995 | Greenwald ................................ 482/91 |
| 5,407,420 | 4/1995 | Bastyr et al. . |
| 5,417,643 | 5/1995 | Taylor ...................................... 601/33 |
| 5,503,619 | 4/1996 | Bonutti . |
| 5,520,181 | 5/1996 | Kreidler et al. ...................... 128/653.5 |
| 5,848,979 | 12/1998 | Bonutti et al. ............................. 601/5 |
| 5,919,148 | 7/1999 | Marko et al. ............................ 600/595 |

OTHER PUBLICATIONS

Copy of Advertising materials from the Internet on Jun. 5, 1998 entitled: "Quadrant by Smith & Nephew DonJoy". "Entering a New Plane".

Copy of Advertising materials from the Internet on Jun. 5, 1998 entitled: "Quadrant Make DonJoy's Quadrant Your First Choice For Effective Post–Operative Shoulder Treatment." "Quadrant Brace Specifications".

Copy of Advertising materials from the Internet on Jun. 5, 1998 entitled: "ULTRASLINGTM bt DONJOY".

*Primary Examiner*—Kim M. Lee
*Attorney, Agent, or Firm*—Tarolli, Sundheim, Covell, Tummino & Szabo L.L.P.

[57] ABSTRACT

A shoulder orthosis is utilized to effect relative movement between bones in a body of a patient. The orthosis includes a base section which is connected with a trunk of a patient's body, an upper arm section which is connected with an upper portion of an arm of the patient, and a lower arm section which is connected with a lower portion of the arm of a patient. An interconnection between the base section and upper arm section of the orthosis is disposed beneath an axilla between the trunk and arm of the patient. A main drive assembly is operable to rotate the lower arm section of the orthosis is relative to the upper arm section of the orthosis to pivot a humerus bone in the upper arm of the patient relative to a scapula bone in a shoulder of the patient. A secondary drive assembly is operable to move the lower arm section and upper arm section relative to the base section of the orthosis to move the upper arm of the patient into alignment with the shoulder of the patient.

134 Claims, 6 Drawing Sheets

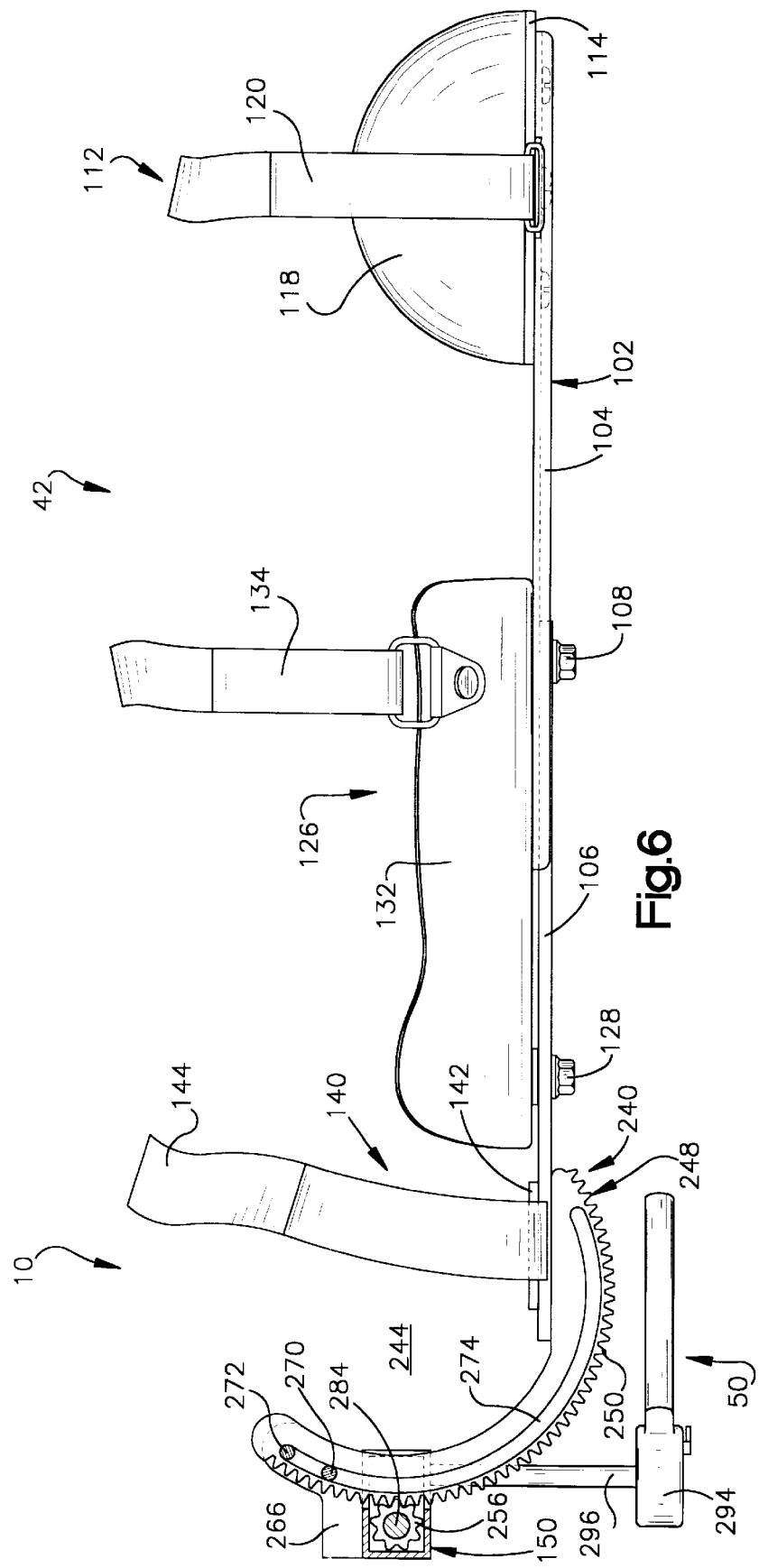

SHOULDER ORTHOSIS

BACKGROUND OF THE INVENTION

The present invention relates to an apparatus for use in effecting relative movement between bones in a body of a patient and, more specifically, to an apparatus for effecting movement of bones in an arm of the patient relative to a shoulder of the patient.

An orthosis for stretching viscoelastic or soft tissue in a human body to regain joint movement and eliminate tissue contracture is disclosed in U.S. Pat. No. 5,285,773. The apparatus disclosed in this patent includes a pair of cuffs which are mounted on cuff arms. A drive assembly interconnects the cuff arms.

Another orthosis is disclosed in U.S. Pat. No. 5,503,619. The orthosis disclosed in this patent includes a pair of cuffs which are connected with cuff arms. A drive assembly interconnects the cuff arms. The orthosis disclosed in the aforementioned U.S. Pat. No. 5,503,610 is particularly well adapted for use in bending a patient's wrist.

An orthosis for effecting relative movement between bones in an arm of a patient is disclosed in U.S. patent application Ser. No. 08/683,196, filed Jul. 18, 1996 now U.S. Pat. No. 5,848,979 by Peter M. Bonutti et al. and entitled "Orthosis". The orthosis disclosed in the aforementioned U.S. patent application includes a first cuff which grips a wrist portion of the arm of a patient. A second cuff grips an upper portion of the arm of the patient. A drive assembly is provided to rotate the first cuff about an axis which extends along the lower portion of the arm of the patient. Operation of the drive assembly effects pronation and suppination of the hand of the patient.

SUMMARY OF THE INVENTION

A new and improved apparatus for effecting relative movement between bones in a body of a patient includes a first cuff which grips a lower portion of an arm of the patient. A second cuff grips an upper portion of the arm of the patient. A drive assembly is operable to rotate the first cuff and a humerus bone in the arm of the patient about a central axis of the humerus bone. This results in a stretching of viscoelastic tissue connected with a head end portion of the humerus bone.

The extent of stretching of the viscoelastic tissue connected with a humerus bone in the arm of the patient may be maximized by interrupting operation of the drive assembly to allow the viscoelastic body tissue to relax. After the viscoelastic body tissue has relaxed, the drive assembly is again operated to further rotate the first cuff and further stretch the viscoelastic body tissue connected with the humerus bone.

A secondary drive assembly is provided to pivot the humerus bone in the arm of the patient about the head end portion of the humerus bone. This moves an arcuate surface on the head end portion of the humerus bone into alignment with an arcuate surface of a glenoid cavity in a scapula bone in the shoulder of the patient. The secondary drive assembly is disposed beneath an axilla between the trunk and arm of the patient.

BRIEF DESCRIPTION OF THE DRAWINGS

The foregoing and other features of the present invention will become more apparent upon a consideration of the following description taken in connection with the accompanying drawings wherein:

FIG. 6. is a fragmentary elevational view, taken generally along the line 6—6 of FIG. 3, illustrating a lower cuff arm and a portion of the main drive assembly in the shoulder orthosis of FIGS. 1–3.

DESCRIPTION OF ONE SPECIFIC PREFERRED EMBODIMENT OF THE INVENTION

General Description

Figure 1:
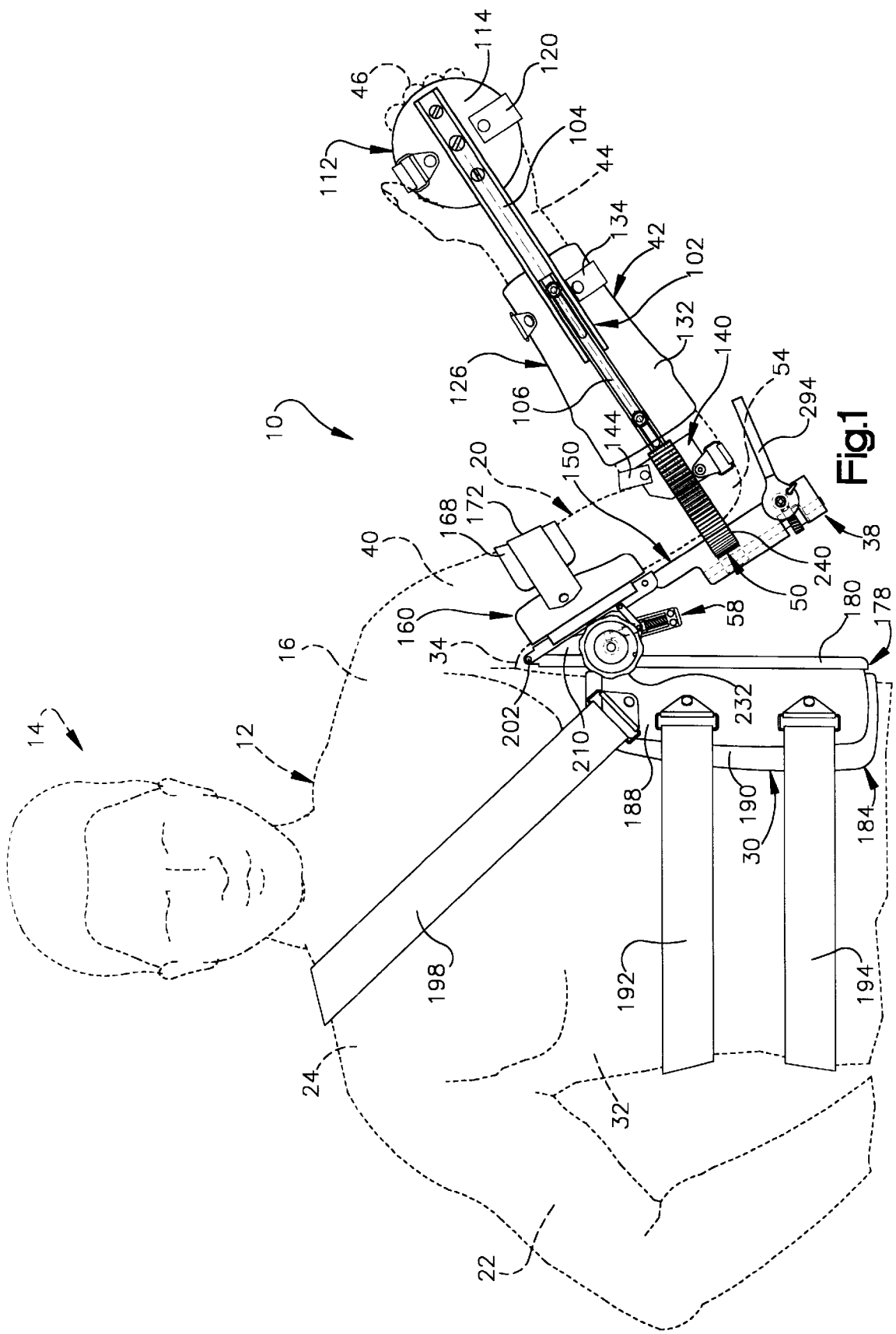
FIG. 1 is a schematic pictorial illustration depicting the manner in which a shoulder orthosis constructed in accordance with the present invention is connected with an arm and trunk of a body of a patient.

A shoulder brace or orthosis 10 (FIGS. 1–3) effects relative movement between bones in a body 12 (FIG. 1) of a patient 14. The shoulder orthosis 10 is used to correct misalignment or malfunction of joints in a shoulder 16 of a patient. Although the shoulder orthosis 10 has been illustrated in FIG. 1 as being utilized in association with a left arm 20 and shoulder 16, the shoulder orthosis 10 could be constructed for use with a right arm 22 and shoulder 24 of the patient 14 if desired.

The shoulder orthosis 10 includes a base section 30 (FIGS. 1–3) which is connected with a trunk 32 (FIG. 1) of the patient's body. The base section 30 is connected with the trunk 32 of the patient's body at a location beneath an armpit or axilla 34. The axilla 34 is formed at the connection between the left arm 20 and left shoulder 16.

The shoulder orthosis 10 includes an upper arm section 38 (FIGS. 1–3) which is connected with the upper arm section 40 (FIG. 1) of the left arm 20 of the patient. A lower arm section 42 (FIGS. 1–3) of the shoulder orthosis 10 is connected with a lower arm section 44 (FIG. 1) of the left arm 20 and a hand 46 of the patient 14.

A main drive assembly 50 (FIGS. 1–3) interconnects the upper arm section 38 and the lower arm section 42. The main drive assembly 50 is manually operable by the patient 14 (FIG. 1) to move the lower section 44 of the arm 20 relative to the upper section 40 of the arm 20. The main drive assembly 50 is located adjacent to an elbow 54 which interconnects the upper and lower sections 40 and 44 of the arm 20.

The main drive assembly 50 is operable to rotate bones in the arm 20 of the patient 14 relative to the shoulder 16 of the patient. Operation of the main drive assembly 50 rotates the bones in the arm 20 of the patient 14 about a longitudinal central axis of the upper arm section 40. The main drive assembly 50 can be operated in any one of two directions to effect either internal or external rotation of a humerus bone in upper arm section 40 relative to the shoulder 16.

A secondary drive assembly 58 (FIGS. 1–3) is manually operable by the patient 14 to align the upper section 40 (FIG.

1) of the arm 20 of the patient 14 with the Shoulder 16 of the patient. The secondary drive assembly 58 is operable in either one of two directions to effect either abduction or adduction of the arm 20.

The secondary drive assembly 58 is located beneath the armpit or axilla 34. The secondary drive assembly is positioned between the upper arm section 40 and the trunk 32 of the patient 14. The secondary drive assembly 58 is operable to move the upper arm section 40 into alignment with the shoulder 16 of the patient 14. The secondary drive assembly 58 is then effective to hold the upper arm section 40 in alignment with the shoulder 16.

In accordance with a feature of the present invention, the shoulder orthosis 10 (FIG. 1) obtains release of soft tissue in the shoulder 16 and/or arm 20 of the patient. The shoulder orthosis 10 effects elongation of viscoelastic tissue connected with the upper arm section 40 and the shoulder 16 of the patient. To effect stretching of the viscoelastic body tissue interconnecting the upper arm section 40 and shoulder 16, the main drive assembly 50 is operated to rotate the humerus bone 62 (FIG. 4) in the upper arm section 40 relative to the shoulder 16.

Operation of the main drive assembly 50 (FIG. 1) to rotate the humerus bone 62 (FIG. 4) is interrupted when the viscoelastic body tissue has been stretched to a maximum extent compatible with a patient's comfort level. The main drive assembly 50 is advantageously operated by the patient 14 himself/herself so that the patient can interrupt operation of the drive assembly when required in order to maintain patient comfort.

The main drive assembly 50 (FIG. 1) is constructed so that it continuously transmits force and is not operated in a reverse direction upon interruption of operation of the main drive assembly by the patient 14. This results in tension being maintained in the viscoelastic body tissue interconnecting the upper section 40 of the arm 20 of the patient 14 and the shoulder 16 when operation of the main drive assembly 50 is interrupted. When a sufficient period of time to enable the viscoelastic tissue to relax has elapsed, the patient 14 again operates the main drive assembly 50 to further stretch the viscoelastic body tissue connected with the upper arm section 40 and shoulder 16.

The shoulder orthosis 10 effects some distraction of the joint between the upper arm section 40 and shoulder 16. This distraction occurs due to the combined weight of the shoulder orthosis 10 and the arm 20.

Bones

Figure 4:
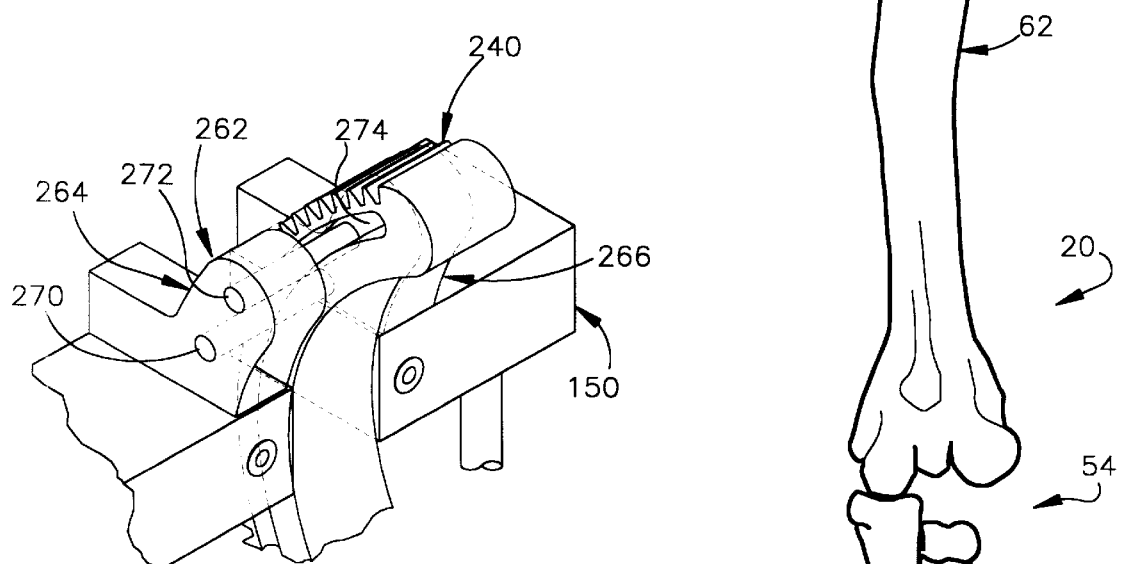
FIG. 4 is a schematic illustration depicting bones in an arm and shoulder of a patient.

Some of the bones in the body 12 of the patient 14 are illustrated in FIG. 4. The trunk 32 of the patient includes a shoulder joint 66 where the upper arm section 40 of the patient is connected with the trunk 32 of the patient. A head end portion 68 of the humerus bone 62 in the upper arm section 40 is connected with the trunk 32 at the shoulder joint 66. A radius bone 72 and an ulna bone 74 in the lower arm section 44 are connected with the opposite or lower end of the humerus bone 62.

The head end portion 68 of the humerus bone 62 is received in a glenoid cavity or fossa 80 formed in a scapula bone 82 at the shoulder joint 66. The scapula bone 82 articulates with the head end portion 68 of the humerus and the clavicle bone 84. The clavicle or collarbone 84 articulates with the sternum 86 and scapula bone 82. The scapula bone 82 is connected with rib bones 88 by body tissue.

The shoulder joint 66 is somewhat similar to a ball and socket joint. The head end portion 68 of the humerus bone 62 has a configuration which may be considered as being hemispherical. The glenoid cavity 80 forms a socket for the head end portion 68 of the humerus bone 62. However, the socket formed by the glenoid cavity 80 is shallow. Therefore, the glenoid cavity 80 may be considered as being a portion of a hemisphere.

It is well known that the head end portion 68 of the humerus bone 62 has an arcuate outer side surface which is not truly hemispherical in configuration. Similarly, the glenoid cavity 80 has a configuration which may be considered as being generally ovate. Since the head end portion 68 of the humerus bone 62 and the glenoid cavity 80 are not true hemispheres, the motion which occurs between the bones at the shoulder 16 during movement of the arm 20 is far more complicated than a simple ball and socket analogy.

A normal shoulder joint 66 which functions in a proper manner can accommodate movement in all directions. In order to obtain motion of the head end portion 68 of the humerus bone 62 without movement of the scapula bone 82 and/or clavicle bone 84, a longitudinal central axis of the humerus bone 62 should be aligned with a central portion of the glenoid cavity 80. When the humerus bone 62 is aligned with the glenoid cavity 80, the longitudinal central axis of the humerus bone extends through or close to the center of the glenoid cavity. At this time, an arcuately curving, generally hemispherical outer side surface 92 on the head end portion 68 of the humerus bone 62 is aligned with and is closely adjacent to a generally hemispherical side surface 94 of the glenoid cavity 80.

It should be understood that the outer side surface 92 on the head end portion 68 of the humerus bone 62 and the side surface 94 of the glenoid cavity 80 do not have truly hemispherical configurations and do not have centers of curvature which are exactly coincident when the head end portion 68 of the humerus bone 62 is aligned with the glenoid cavity 80. Therefore, there may be some shifting between the humerus bone 62 and the scapula bone 82 and/or clavicle bone 84 during rotation of the humerus bone 62 about its longitudinal central axis even though the longitudinal central axis of the humerus bone is aligned as close as is reasonably possible with the center of the glenoid cavity 80. In order to obtain stretching of viscoelastic body tissue interconnecting the head end portion 68 of the humerus bone 62 and the scapula bone 82 at the shoulder joint 66, movement of the scapula bone and/or clavicle bone 84 relative to the trunk 32 should be minimized during operation of the shoulder orthosis 10.

Lower Arm Section

The lower arm section 42, (FIGS. 2, 3 and 6) of the shoulder orthosis 10 is connected with) the lower section 44 of the patient's arm 20 (FIG. 1). The lower arm section 42 of the shoulder orthosis 10 (FIGS. 2, 3 and 6) includes a first or lower cuff arm 102. The lower cuff arm 102 includes a straight rigid metal outer channel member 104 and a straight rigid metal inner channel member 106. The outer and inner channel members 104 and 106 are disposed in a telescopic relationship with each other and are interconnected by a fastener 108. When the fastener 108 is released, the outer channel member 104 and inner channel member 106 are longitudinally movable relative to each other to vary the extent of the lower arm section 42 of the orthosis 10.

A hand cuff 112 is disposed on the axially outer end portion of the outer channel member 104. The hand cuff 112 is disposed on a rigid circular metal base 114. The base 114 is fixedly connected with the outer channel member 104. A flexible hemisphere 118 (FIG. 6) is connected to the metal base 114 and engages a palm of a hand 46 (FIG. 1) of the patient. A strap 120 (FIGS. 2, 3 and 6) engages the back of the hand 46 of the patient. The strap 120 presses the palm of the patient's hand against the hemisphere 118. By loosening the fastener 108, the position of the hemisphere 118 relative to the inner channel member 106 can be varied to adjust the lower cuff arm 102 to accommodate patients having arms of different lengths.

The hemisphere 118 (FIGS. 2 and 6) has a radius which is sufficient to enable a portion of the palm of the patient's hand 46 (FIG. 1) to be further from the lower cuff arm 102 than a longitudinal central axis of the lower section 44 of the patient's arm 20. This results in the patient's hand 46 being held in a relaxed, cup-shaped configuration. By engaging the hemisphere 118, the patient's hand 46 is held against sidewise movement and the lower arm section 44 is stabilized on the lower arm section 42 of the orthosis 10.

Figure 2:
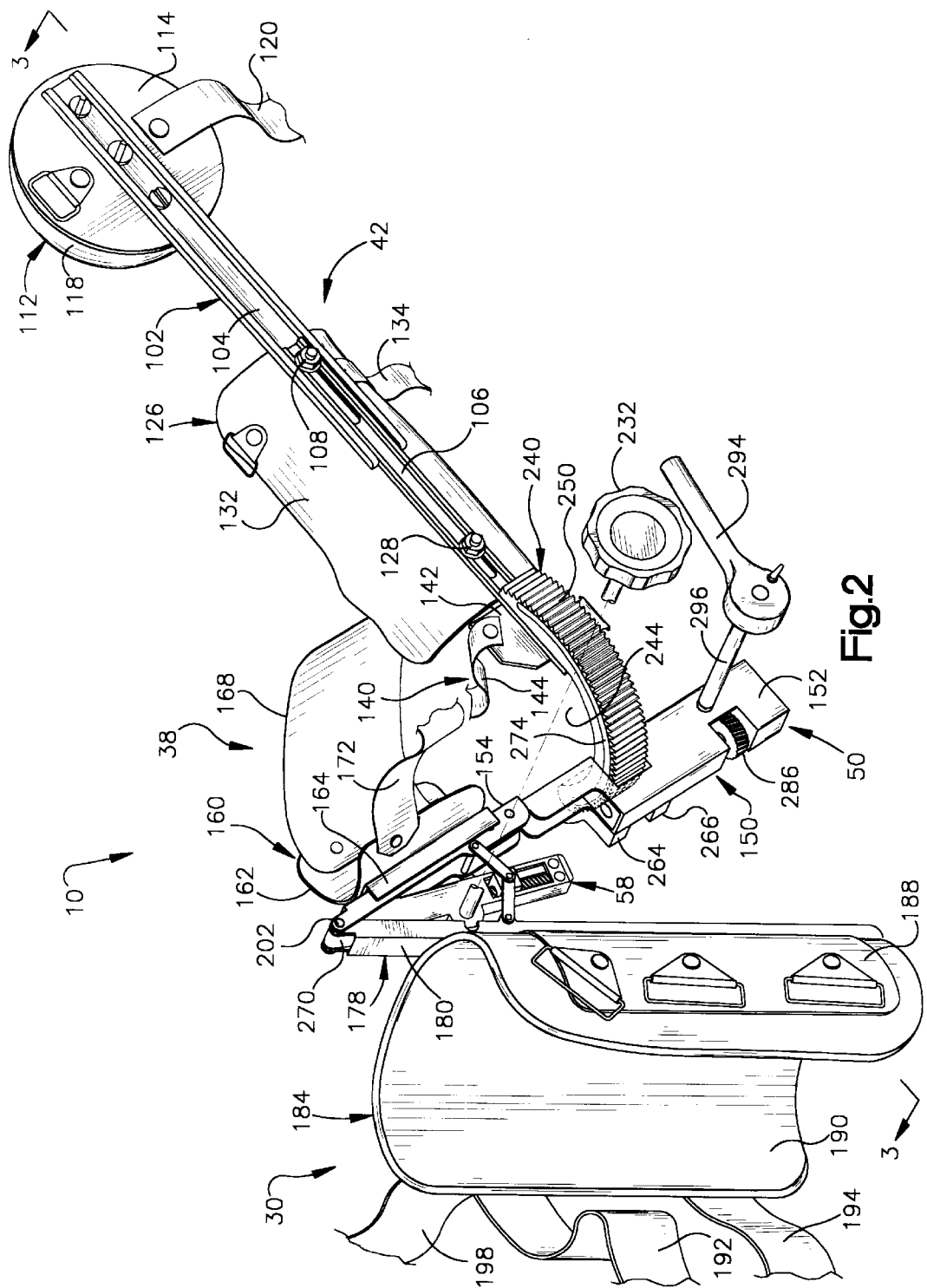
FIG. 2 is an illustration further depicting the construction of the shoulder orthosis of FIG. 1.
Figure 3:
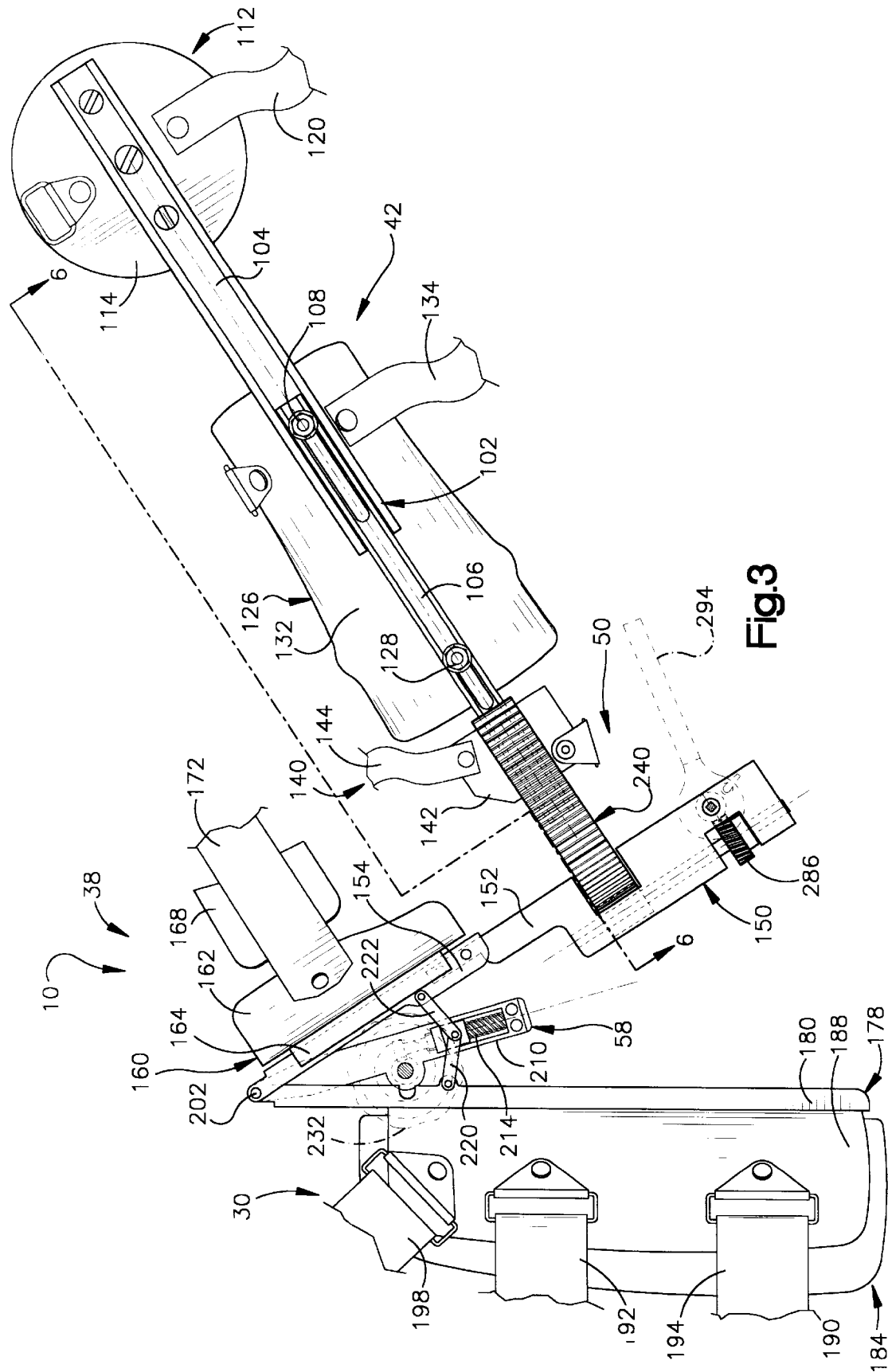
FIG. 3 is a front elevational view, taken generally along the line 3—3 of FIG. 2, further illustrating the construction of the shoulder orthosis.

A first or lower cuff 126 is connected with the inner channel member 106 by the fastener 108 and a second fastener 128 (FIGS. 2, 3 and 6). The lower cuff 126 includes a flexible polymeric body section 132 which is connected to the inner channel member 106 by the fasteners 108 and 128. The body section 132 extends part way around the lower arm section 44 of the patient 14 (FIG. 1). A central axis of the lower cuff 126 extends parallel to the lower cuff arm 102 and extends through the hemisphere 118 in the hand cuff 112.

A strap 134 (FIGS. 2, 3 and 6) is connected with the body section 132 and extends around the lower arm section 44 of the patient. Tightening the strap 134 causes the body portion 132 of the first or lower cuff 126 to flex inward and firmly grip the radius bone 72 and ulna bone 74 (FIG. 4) in the lower arm section 44 of the patient 14 (FIG. 1). Although one specific construction for the lower cuff 126 and hand cuff 112 is illustrated in FIGS. 2, 3 and 6, it is contemplated that these cuffs could have a different construction if desired.

In addition, the lower arm section 42 includes an elbow cuff 140 (FIGS. 2, 3 and 6) which is mounted on the inner channel member 106. The elbow cuff 140 includes a base plate 142 against which the elbow 54 (FIG. 1) in the arm 20 of the patient is pressed by a strap 144. When the strap 144 is tightened, the elbow 54 is firmly held against movement relative to the lower arm section 42. The elbow cuff 140 could have a different construction or could be omitted if desired.

The lower section 44 (FIG. 1) of the arm 20 of the patient 14 is firmly held against movement relative to the lower cuff arm 102 by three different cuffs. Thus, the hand cuff 112 holds the hand 46 of the patient 14 against movement relative to the lower cuff arm 102. The first or lower cuff 126 holds the lower arm section 44 of the arm 20 of the patient 14 against movement relative to the lower cuff arm 102. In addition, the elbow cuff 140 holds the elbow 54 of the patient 14 against movement relative to the lower cuff arm 102.

When the first or lower cuff 126 is connected with the lower section 44 of the arm 20 of the patient 14 and the hand cuff 112 is connected with the hand 46 of the patient (FIG. 1), a central axis of the lower section of the arm of the patient extends through the hemisphere 118. Force is transmitted between the hemisphere 118 and palm of the hand 46 of the patient during operation of the shoulder orthosis 10 to effect external rotation of the arm 20 of the patient. Similarly, force is transmitted between the strap 120 and the back of the hand 46 of the patient during operation of the shoulder orthosis 10 to effect internal rotation of the arm 20 of the patient.

Although specific constructions for the hand cuff 112, lower cuff 126 and elbow cuff 140 have been disclosed herein, it is contemplated that these cuffs could have a different construction if desired. For example, the base plate 142 of the elbow cuff 140 could be integrally formed as one piece with the body section 132 of the lower cuff. There are many other known cuff constructions which could be used in place of the specific cuff constructions disclosed herein. If desired, the lower cuff arm 102 could be formed as a portion of the lower cuff 126.

Upper Arm Section

The upper arm section 38 (FIG. 1) of the shoulder orthosis 10 is connected with the upper section 40 of the patient's arm 20. The upper arm section 38 (FIGS. 2, 3 and 5) includes a second or upper cuff arm 150. The upper cuff arm 150 has a longitudinal axis which extends perpendicular to a longitudinal axis of the lower cuff arm 102.

The second or upper cuff arm 150 includes a rigid straight metal lower channel member 152 (FIG. 5) and a rigid straight metal upper channel member 154. The lower and upper channel members 152 and 154 are telescopically adjustable relative to each other to accommodate patients having different length upper arm portions. Pin members 156 are provided to fixedly interconnect the lower and upper channel members 152 and 154 when the second or upper cuff arm 150 has been adjusted to a desired length.

Figure 5:
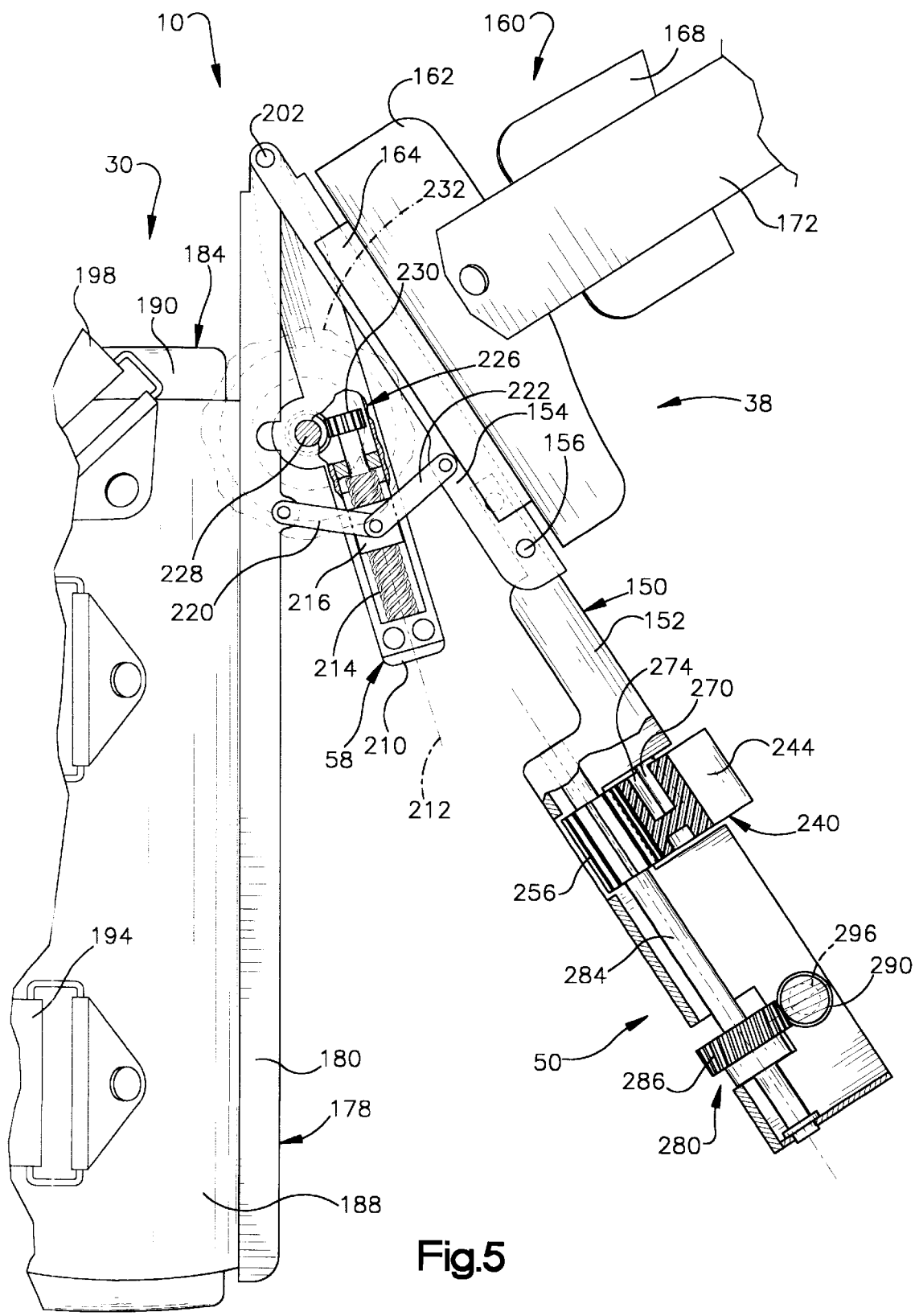
FIG. 5 is an enlarged fragmentary front elevational view of a portion of the shoulder orthosis of FIGS. 1–3, illustrating the manner in which a main and secondary drive assembly are connected with cuff arms.

The upper section 40 of the patient's arm 20 (FIG. 1) is connected with the second or upper cuff arm 150 by an upper cuff 160 (FIGS. 2, 3 and 5). The upper cuff 160 has a longitudinal central axis which extends perpendicular to and intersects a longitudinal central axis of the lower cuff 126. The upper cuff 160 includes a flexible polymeric body section 162. The body section 162 is fixedly connected to a connector channel 164. The connector channel 164 is fixedly connected to the upper channel member 154 of the upper cuff arm 150.

A flexible plastic tongue 168 (FIG. 2) is connected with the body section 162 of the upper cuff 160. A strap 172 is connected with the opposite side of the body section 162. The flexible tongue 158 is positioned in engagement with the upper section 40 of the patient's arm 20 (FIG. 1). The strap 172 is tightened to securely grip the upper section 40 of the patient's arm with the upper cuff 160.

Although one specific upper cuff 160 has been illustrated in FIGS. 2, 3 and 5, it is contemplated that the upper cuff 160 could have a different construction if desired. The upper cuff arm 150 could also have a construction which is different than the specific construction illustrated in the drawings. If desired, the upper cuff 160 could be constructed in such a manner as to enable the upper cuff arm 150 to be formed as a portion of the upper cuff.

Base Section

The base section 30 (FIGS. 1, 2 and 3) of the shoulder orthosis 10 is connected with and is held against movement relative to the trunk 32 (FIG. 1) of the patient. The base section 30 of the orthosis 10 includes a third or base cuff arm 178 (FIGS. 1, 2 and 3). The base cuff arm 178 is formed by a single rigid straight metal channel member 180.

A third or base cuff 184 is slidably connected with slots in the base cuff arm 178 by suitable fasteners (not shown). The fasteners enable the base cuff 184 to be released for movement axially along the base cuff arm 178 to position the base cuff 184 for engagement with the trunk 32 of different size patients 14. The base cuff 184 includes a body section 188 which is formed of a flexible polymeric material. A pad 190 is connected with the body section 188. The body section 188 and pad 190 grip the trunk 32 of the patient at a location below the arm pit or axilla 34 (FIG. 1).

The body section 188 of the third or base cuff 184 is connected with the trunk 32 of the patient 14 by a pair of generally horizontal straps 192 and 194 (FIG. 1). The straps 192 and 194 extend around the trunk 32 of the patient and are connected with opposite sides of the body section 188 of the base cuff 184. A shoulder strap 198 extends across the shoulder 24 to hold the body section 188 of the base cuff 184 in position on the trunk 32 of the patient 14. The straps 192, 194, and 198 cooperate with the body section 188 of the base cuff 184 to hold the base cuff stationary on the trunk 32 of the patient 14.

The base cuff arm 178 and the second or upper cuff arm 150 are interconnected at a pivot connection 202 (FIGS. 1, 2, 3 and 5). The pivot connection 202 enables the upper cuff arm 150 to pivot about an axis which extends perpendicular to and intersects longitudinal central axes of the base cuff arm 178 and the second or upper cuff arm 150. The pivot connection 202 is positioned immediately beneath the armpit or axilla 34 (FIG. 1) on the body 12 of the patient 14. The pivot connection 202 enables the upper arm section 38, main drive assembly 50, and lower arm section 42 to be moved as a unit relative to the base section 30 of the orthosis 10 by operation of the secondary drive assembly 58.

The base cuff 184 could have a construction which is different than the specific construction disclosed herein. For example, the base cuff 184 could be integrally formed as one piece with the upper cuff 160. If desired, the base cuff arm 178 could be formed as a portion of the base cuff 184.

Secondary Drive Assembly

The secondary drive assembly 58 (FIG. 1) moves the upper arm section 40 and the lower arm section 44 of the arm 20 of the patient 14 relative to the shoulder 16. The secondary drive assembly 58 is operated to align the central axis of the humerus bone 62 (FIG. 4) in the upper arm section 40 with the center of the glenoid cavity 80 in the scapula bone 82. The secondary drive assembly 58 may be operated by either a therapist or the patient 14. In order to promote patient confidence, it may be preferred to have the patient 14 operate the secondary drive assembly under the instruction of a therapist.

When the central axis of the humerus bone extends through a central portion of the glenoid cavity 80, the humerus bone 62 can be rotated about its central axis while the scapula bone 82 and clavicle bone 84 remain substantially stationary relative to the trunk 32 of the patient 14. This is because when the humerus bone 62 is aligned with the center of the glenoid cavity 80, the central axis of the humerus bone 62 extends through a center of curvature of an arcuate surface 92 on the head end portion 68 of the humerus bone 62 and through a center of curvature of an arcuate surface 94 of the glenoid cavity 80.

To move the humerus bone 62 into alignment with the glenoid cavity 80, the secondary drive assembly 58 includes a rectangular tower or base frame 210 (FIG. 5). The tower or base frame 210 extends downward from the pivot connection 202 between the base cuff arm 178 and the second or upper cuff arm 150. The base cuff arm 178 and second or upper cuff arm 150 are pivotal toward and away from the tower 210 about the pivot connection 202.

The tower 210 has a central axis 212 (FIG. 5) which bisects an angle formed between the longitudinal central axis of the base cuff arm 178 and the longitudinal central axis of the second or upper cuff arm 150. The longitudinal central axis 212 of the tower 210 intersects and extends perpendicular to the axis about which the base cuff arm 178 and second or upper cuff arm 150 are pivotal at the pivot connection 202.

The secondary drive assembly 58 includes a screw 214 (FIG. 5) having a central axis which is coincident with the central axis 212 of the tower 210. The screw 214 is rotatably supported in the tower 210 by suitable bearings. The screw 214 has an external thread which engages an internal thread on an actuator block 216. The cooperation between the external thread on the screw 214 and the internal thread between the actuator block 216 results in the actuator block moving toward or away from the pivot connection 202 during rotation of the screw 214 about its central axis.

A pair of identical links 220 and 222 (FIG. 5) extend between the actuator block 216 and the cuff arms 178 and 150. As the actuator block 216 is moved axially along the screw 214, the links 220 and 222 maintain the actuator block and the screw 214 centered midway between the cuff arms 178 and 150. Although only a single pair of links 220 and 222 are shown in FIG. 5, it should be understood that a second pair of links having the same construction as the links 220 and 222 are connected with the rear or posterior side of the actuator block 216 and the cuff arms 178 and 150. The links on the posterior or rear side of the actuator block 216 are aligned with the links 220 and 222 on the front or anterior side of the actuator block.

A manually operable drive assembly 226 (FIG. 5) is connected with the screw 214. The drive assembly 226 includes a worm 228 which engages a gear 230. The gear 230 is fixedly connected with the screw 214. The worm 228 is rotatable about an axis which extends perpendicular to coincident central axes of the gear 230 and screw 214.

Manual rotation of an input member or knob 232 (FIGS. 1 and 2) rotates the worm 228 (FIG. 5) and the gear 230. Rotation of the gear 230 rotates the screw 214. Rotation of the screw 214 moves the actuator block 216 either toward or away from the pivot connection 202. When the actuator block 216 is moved toward the pivot connection 202 by the screw 214, the base cuff arm 178 and upper cuff arm 150 are pivoted away from each other by the links 220 and 222. When the actuator block 216 is moved away from the pivot connection by the screw 214, the base cuff arm 178 and upper cuff arm 150 are pivoted toward each other by the links 220 and 222.

The input member 232 can be manually rotated by the patient 14 to adjust the extent of abduction of the arm 20 (FIG. 1) to a position of greatest comfort. The position of greatest comfort will correspond to the position in which the longitudinal central axis of the humerus bone 62 (FIG. 4) is aligned with the center of the glenoid cavity 80.

The secondary drive assembly 58 (FIG. 5) is constructed so that once the angle between the upper cuff arm 150 and the base cuff arm 178 has been adjusted by operation of the secondary drive assembly, the angle between the cuff arms is maintained constant. Thus, the secondary drive assembly is constructed so that force applied to the base cuff arm 178 and upper cuff arm 150 cannot actuate the secondary drive assembly 58 to change the angle, between the cuff arms. Therefore, once the central axis of the humerus bone has been aligned with the center of the glenoid cavity 80 by operation of the secondary drive assembly 58, the humerus bone 62 is maintained in alignment with the center of the glenoid cavity.

The secondary drive assembly 58 has a construction which is generally similar to the construction of a drive assembly disclosed in U.S. Pat. No. 5,285,773. If desired, the secondary drive assembly 58 could have a different construction. For example, the secondary drive assembly 58 could be constructed in a manner similar to that disclosed in U.S. Pat. No. 5,503,619. Of course, other known drive assemblies could be substituted for the specific secondary drive assembly 58 illustrated in FIG. 5.

Main Drive Assembly

The main drive assembly 50 (FIGS. 2 and 5) interconnects the upper cuff arm 150 and the lower cuff arm 102. The arm 20 (FIG. 1) of the patient 14 is bent at a 90° angle at the elbow 54. This allows upper section 20 of the patient's arm 20 to extend along the upper cuff arm 150. The lower section 44 of the patient's arm 20 extends along the lower cuff arm 102. The elbow 54 and adjacent portions of the patient's arm 20 extend through the main drive assembly 50.

The main drive assembly 50 is operable to effect either internal or external rotation of the humerus bone 62 (FIG. 4) in the upper arm section 40 of the arm 20 relative to the shoulder joint 66 and scapula bone 82. Operation of the main drive assembly 50 rotates the humerus bone 62 about its longitudinal central axis. To effect rotation of the humerus bone 62, the main drive assembly 50 pivots the lower cuff arm 102 and lower section 44 of the patient's arm 20 about the longitudinal central axis of the humerus bone. The upper cuff arm 150 and base cuff arm 178 are stationary relative to each other and the trunk 32 of the patient 14 during operation of the main drive assembly 50 and movement of the lower cuff arm 102.

When the main drive assembly 50 is operated to rotate the humerus bone 62 about its longitudinal central axis, the secondary drive assembly 58 will have previously been adjusted to align the longitudinal central axis of the humerus bone with the center of the glenoid cavity 80. Therefore, when the humerus bone 62 is rotated about its central axis, there is no substantial movement of the scapula bone 82 and/or clavicle bone 84 relative to each other and the trunk 32 of the patient 14. It should be understood that the main drive assembly 50 is not operated to rotate the humerus bone 62 until after the secondary drive assembly 58 has been operated to position the humerus bone in alignment with the glenoid cavity 80.

The main drive assembly 50 includes a main gear or drive member 240 which is fixedly connected with the lower cuff arm 102 (FIGS. 3 and 6). The main gear or drive member 240 is rotatably connected with the upper cuff arm 150. When the orthosis 10 is positioned on the arm 20 of a patient 14, in the manner illustrated in FIG. 1, the arm of the patient extends through an opening 244 (FIGS. 2 and 6) in the main gear 240. Thus, the elbow 54 (FIG. 1) is disposed in the opening 244 (FIG. 6) in the main gear 240. The elbow cuff 140 holds the elbow in position relative to the main gear 240 and lower cuff arm 102.

Although the elbow 54 is shown in FIG. 1 as being disposed in the opening 244 in the main gear 240, a different portion of the arm 20 of the patient 14 could be disposed in the opening if desired. Furthermore, it is contemplated that the main gear 240 could be offset to one side, for example, downward, of the elbow 54 and rotatably connected with the upper cuff arm 150. If this was done, the arm 20 of the patient 14 would not extend through the main gear 240 and the opening 244 could be eliminated. However, it is preferred to have the main gear 240 as close as possible to the elbow 54 and lower cuff arm 102 to promote efficient transfer of force between the main drive assembly 50 and the arm 20 of the patient 14.

The main gear 240 includes an arcuate array 248 (FIG. 6) of gear teeth 250. The arcuate array 248 of gear teeth has a configuration of a portion of a circle. The central axis of the main gear 240 extends parallel to the longitudinal central axis of the upper cuff arm 150 and is coincident with a longitudinal central axis of the upper section 40 (FIG. 1) of the arm 20 of the patient. The opening 244 extends between opposite ends of the arcuate array 248 of gear teeth 250 to enable the arm 20 (FIG. 1) of the patient 14 to be readily moved into the opening in the main gear.

The inner channel member 106 (FIG. 6) of the lower cuff arm 102 extends into the opening 244. The inner channel member 106 is fixedly connected with the main gear 240 by suitable fasteners (not shown) which extend through the base plate 142 of the elbow cuff 140. The inner channel member 106 is fixedly connected to the main gear 240 with a central axis of the inner channel member extending perpendicular to the parallel central axes of the main gear and upper cuff arm 150. Since the lower cuff arm 102 is fixedly connected with the main gear 240, the lower cuff arm rotates with the main gear relative to the upper cuff arm 150.

When the arm 20 of the patient 14 is positioned in the upper cuff 160, opening 244 in the main gear 240, and lower cuff 126, in the manner illustrated in FIG. 1, the central axis of the humerus bone 62 is substantially coincident with a central axis of the arcuate array 248 of gear teeth 250 (FIG. 6). The central axis of the lower section 44 (FIG. 1) of the patient's arm 20 intersects the central axis of the upper section 40 of the patient's arm at a right angle at the elbow 54. The intersection of the central axis of the upper section 40 and lower section 44 of the patient's arm 20 is disposed in a central portion of the opening 244 in the main gear 240. When the main gear 240 and lower cuff arm 102 are rotated about the central axis of the main gear, the humerus bone 62 (FIG. 4) in the upper section 40 of the arm 20 of the patient is rotated about its central axis.

The main gear 240 is disposed in meshing engagement with a pinion gear 256 (FIGS. 5 and 6). The pinion gear 256 is rotatably mounted on the upper cuff arm 150.

Figure 7:
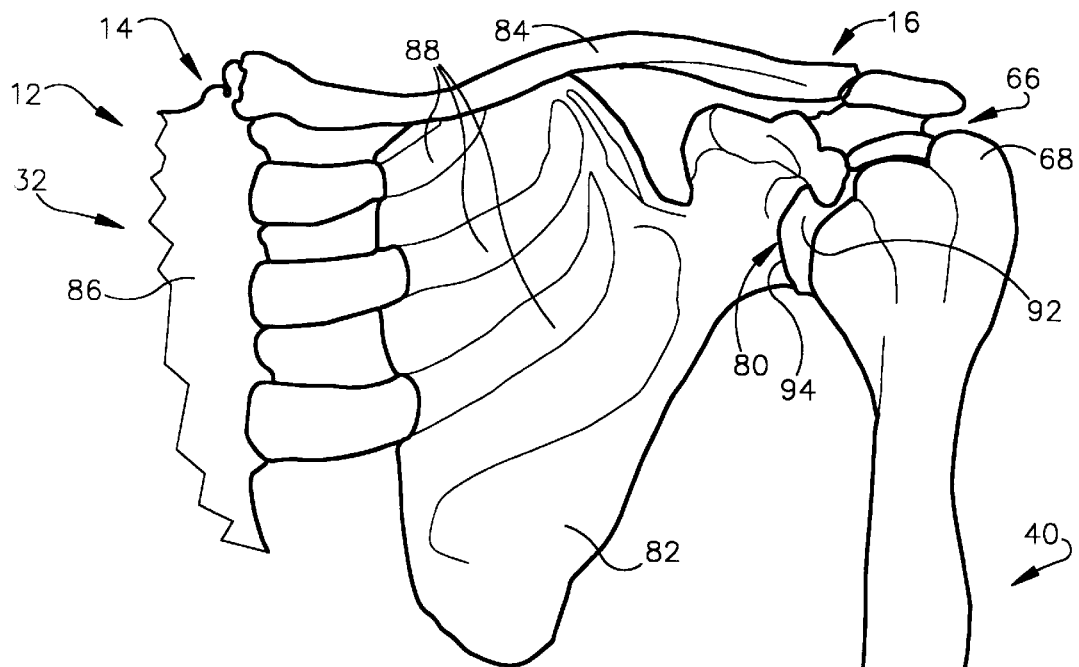
FIG. 7 (on sheet 4 of the drawings) is a fragmentary pictorial illustration of the manner in which a main gear in the drive assembly is mounted on a cuff arm of the orthosis of FIGS. 1–3.

The main gear 240 is supported for rotation about the central axis of the opening 244 and the central axis of the upper arm section 40 of the arm 20 (FIG. 1) of the patient 14 by a positioning assembly 262 (FIG. 7). The positioning assembly 262 is disposed on the anterior or back side of the main cuff arm 150. The positioning assembly 262 includes a pair of guide blocks 264 and 266 (FIG. 7) which engage axially opposite sides of the main gear 240.

The guide blocks 264 and 266 are fixedly mounted on the upper cuff arm 150. A pair of parallel pins 270 and 272 extend from the guide block 262 into an arcuate groove 274 (FIGS. 6 and 7) formed in the main gear 240. The pins 270 and 272 extend into the arcuate groove 274 to guide rotational movement of the main gear 240 relative to the upper cuff arm 150 upon rotation of the pinion gear 256 (FIG. 6). Although a groove 274 (FIG. 7) is formed in only one side of the main gear 240 and pins 270 and 272 extend from only the guide block 264, it is contemplated that a second groove could be formed in the axially opposite side of the main gear 240 and be engaged by pins extending from the guide block 266 if desired.

It should be understood that a different mounting arrangement could be utilized for supporting the main gear 240. Thus, rather than having the arcuate groove 274, a pair of arcuate ribs could be provided on opposite sides of the main gear. These ribs would extend into arcuate tracks formed in the guide blocks 264 and 266. By having the support for the main gear 240 offset from the central axis of the main gear, it is possible to have a portion of the arm 20 (FIG. 1) of the patient 14 extend into the opening 244 (FIG. 2) through the central portion of the main gear 240. However, the main gear 240 could be offset to one side of the arm of the patient and could be rotatably supported at its center if desired.

To rotate the main gear 240 and lower cuff arm 102 relative to the second or upper cuff arm 150, the pinion gear 256 is rotated by a pinion drive 280 (FIG. 5). The pinion drive 280 includes a drive shaft 284 (FIG. 5) which is fixedly connected with the pinion gear 256. A second pinion gear 286 is fixedly connected to the drive shaft 284 in a coaxial relationship with the pinion gear 256. A worm 290 is disposed in meshing engagement with the second pinion gear 286.

The worm 290 is driven by a reversible ratchet 294 (FIG. 2). The reversible ratchet 294 is connected with the worm 290 by an input shaft 296. The ratchet 294 extends in the anterior direction, that is frontward, from the upper cuff arm 150. This enables the ratchet 294 to be manually operated by the patient 14.

The patient operates the main drive assembly 50 by actuating the ratchet 294 under the influence of force transmitted from the right arm 22 (FIG. 1) of the patient to the ratchet 294. Of course, a therapist may assist in operation of the ratchet 294 if desired. The reversible ratchet 294 can be actuated to rotate the main gear 240 in either one of two directions to effect either internal or external rotation of the humerus bone 62 in the upper arm section 40 of the patient 14.

Mounting and Operation of the Orthosis

When the orthosis 10 is to be mounted on the patient 14, the straps 192, 194, and 198 for the base cuff 184 (FIG. 1), a strap 144 for the elbow cuff 140, the strap 134 for the lower cuff 126, and the strap 120 for the hand cuff 112 are all released in the manner illustrated in FIG. 2. The body section 188 of the base cuff 184 is then positioned in engagement with the trunk 32 of the patient 14. The straps 192, 194 and 198 are then pulled only tight enough to loosely hold the base cuff 184 in position on the trunk 32 of the patient. At this time, the connection 202 between the base cuff arm 178 and the upper cuff arm 150 is disposed approximately one inch below the arm pit or axilla 34 (FIG. 1) of the patient 14.

Contemporaneously with positioning of the base cuff 184 on the trunk 32 of the patient, the arm 20 of the patient is positioned in the upper cuff 160 and the lower cuff 126. The elbow of the patient is positioned in the elbow cuff 140. The lower cuff 126 is then tightened to grip the lower arm section 44. The elbow cuff 140 and the hand cuff 112 are then tightened. The upper cuff 160 is then tightened.

Once the various cuffs have been tightened to secure the shoulder orthosis 10 to the arm 20 of the patient, the orthosis is adjusted so that the patient's shoulder is 30 degrees scapular plane. The upper arm 40 of the patient extends forward at an angle of approximately 30°. The straps 192, 194 and 198 are then tightened to hold the shoulder orthosis 10 firmly in place.

The input knob 232 of the secondary drive assembly 58 is then actuated to a plane approximately 45° of abduction of the shoulder 16 of the patient. At this time, the arm 20 is positioned in the plane of the scapula. The aforementioned steps may be performed by the patient alone or by the patient with the help of a therapist.

Once the upper section 40 of the arm 20 of the patient has been positioned in alignment with the shoulder 16 by operation of the secondary drive assembly 58, the patient operates the main drive assembly 50 to effect either external or internal rotation of the humerus bone 62 in the upper section 40 of the arm 20. To actuate the main drive assembly 50, the patient 14 manually rotates the ratchet 294 (FIG. 2).

Rotation of the ratchet 294 rotates the worm 290 and drive shaft 284. Rotation of the drive shaft 284 rotates the pinion gear 256 and main gear 240. As the main gear 240 is rotated relative to the upper cuff arm 150, the humerus bone 62 is rotated about its central axis. Rotation of the humerus bone 62 stretches viscoelastic tissue in the shoulder joint 66.

When the patient 14 has operated the main drive assembly 50 to a maximum extent compatible with comfort of the patient, operation of the main drive assembly is interrupted. The drive arrangement between the worm 290 and second gear 286 is such that force transmitted from the lower arm section 44 through the lower cuff arm 102 to the main gear 50 is ineffective to rotate the main gear relative to the upper cuff arm 150. Therefore, tension is maintained in the viscoelastic body tissue connected with the head end portion 68 of the humerus bone 62 even though operation of the main drive assembly 50 is interrupted.

Immediately after operation of the main drive assembly is interrupted, the stretched viscoelastic body tissue connected with the humerus bone 62 begins to relax. With the passage of a relatively short interval of time, for example fifteen minutes, the viscoelastic body tissue will have relaxed sufficiently to enable the patient 14 to again operate the main drive assembly 50 to further stretch the viscoelastic tissue. As the patient operates the main drive assembly 50 to further stretch the viscoelastic body tissue, the main gear 240 and the lower cuff arm are rotated relative to the upper cuff arm 150.

When the patient has again reached the limit of his level of comfort, operation of the drive assembly 50 is interrupted. The process of operating and interrupting the operation of the main drive assembly 50 is repeated to obtain a gradual stretching of the viscoelastic tissue connected with the humerus bone 62. Since the patient is in full control of the operation of the main drive assembly 50, the patient determines the extent of the stretching of the viscoelastic body tissue.

When the viscoelastic body tissue has been repeatedly stretched to the maximum extent allowed by the comfort level of the patient, the shoulder orthosis 10 is removed from the body 12 of the patient 14. To do this, the direction of operation of the ratchet 294 is reversed and the main drive assembly 50 operated to release the pressure against the lower section 44 of the arm 20 of the patient. Once this has been done, the various cuffs are loosened and the orthosis 10 is removed from the patient until the next treatment is undertaken.

Conclusion

A new and improved apparatus 10 for effecting relative movement between bones in a body 12 of a patient 14 includes a first cuff 126 which grips a lower portion 44 of an arm 20 of the patient. A second cuff 160 grips an upper portion 40 of the arm 20 of the patient. A drive assembly 50 is operable to rotate the first cuff 126 and a humerus bone 62 in the arm 20 of the patient 14 about a central axis of the humerus bone. This results in a stretching of viscoelastic tissue connected with a head end portion 68 of the humerus bone 16.

The extent of stretching of the viscoelastic tissue connected with a humerus bone 62 in the arm 20 of the patient 14 may be maximized by interrupting operation of the drive assembly 50 to allow the viscoelastic body tissue to relax. After the viscoelastic body tissue has relaxed, the drive assembly 50 is again operated to further rotate the first cuff 126 and further stretch the viscoelastic body tissue connected with the humerus bone 62.

A secondary drive assembly 58 is provided to pivot the humerus bone 62 in the arm 20 of the patient 14 about the head end portion 68 of the humerus bone. This moves an arcuate surface 92 on the head end portion 68 of the humerus bone 62 into alignment with an arcuate surface 94 of a glenoid cavity 80 in a scapula bone 82 in the shoulder 16 of the patient 14. The secondary drive assembly 58 is disposed beneath an axilla 34 between the trunk 32 and arm 20 of the patient 14.

What is claimed is:

1. An apparatus for use in effecting relative movement between bones in a body of a patient, said apparatus comprising first cuff means for gripping a lower portion of an arm of the patient, second cuff means for gripping an upper portion of the arm of the patient, and drive means connected with said first and second cuff means for rotating said first cuff means about an axis which extends along the upper portion of the arm of the patient, said drive means includes a drive member which is rotatable about the axis which extends along the upper portion of the arm of the patient, said first cuff means being connected with said drive member for rotation therewith, said drive member at least partially defines an opening and a portion of the arm of the patient located between said first and second cuff means is disposed in the opening.

2. An apparatus as set forth in claim 1 wherein said drive means is operable to rotate said first cuff means about the axis which extends along the upper portion of the arm of the patient with an elbow between the upper and lower portions of the arm of the patient bent.

3. An apparatus as set forth in claim 1 further including a first cuff arm connected with said first cuff means and a second cuff arm connected with said second cuff means, said drive means being operable to rotate said first cuff arm and said first cuff together relative to said second cuff arm about the axis which extends along the upper portion of the arm of the patient.

4. An apparatus as set forth in claim 3 further including a third cuff arm connected with said second cuff arm, and third cuff means for connecting said third cuff arm with a trunk of the patient's body.

5. An apparatus as set forth in claim 3 further including second drive means connected with said second and third cuff arms for rotating said first and second cuff arms together relative to said third cuff arm about an axis which extends transverse to the axis which extends along the upper portion of the arm of the patient.

6. An apparatus as set forth in claim 1 further including second drive means connected with said first and second cuff means for rotating said first and second cuff means together about an axis which extends transverse to the axis which extends along the upper portion of the arm of the patient.

7. An apparatus as set forth in claim 1 further including support means which rotatably supports said drive member for rotation about the axis which extends along the upper portion of the arm of the patient, said support means being offset to one side of the axis which extends along the upper portion of the arm of the patient.

8. An apparatus as set forth in claim 1 further including a base member connected with said second cuff means, said drive member being movable along an arcuate path relative to said base member, an arcuate guide surface connected with one of said base and drive members, a follower connected with a second one of said base and drive members and disposed in engagement with said arcuate guide surface, said arcuate guide surface having a center of curvature which is disposed on the axis which extends along the upper portion of the arm of the patient, said follower and guide surface cooperating to guide movement of said drive member along the arcuate path.

9. An apparatus as set forth in claim 1 further including a first cuff arm connected with said first cuff means, and a second cuff arm connected with said second cuff means, said first and second cuff arms being interconnected by said drive means.

10. An apparatus as set forth in claim 9 further including a third cuff arm pivotally connected with said second cuff arm and third cuff means for connecting said third cuff arm with a trunk of the patient's body.

11. An apparatus as set forth in claim 1 wherein said drive includes teeth disposed in an arcuate array which forms only a portion of a circle and has spaced apart end portions, said drive member having an opening which extends between spaced apart end portions of said arcuate array of teeth, said second cuff means being aligned with the opening in said drive member to enable a portion of the arm of the patient to be disposed in the opening in said drive member when the lower portion of the arm of the patient is gripped by said first cuff means and the upper portion of the arm of the patient is gripped by said second cuff means.

12. An apparatus as set forth in claim 11 wherein the axis which extends along the upper portion of the arm of the patient extends through the opening in said drive member and said drive means is operable to rotate said drive member and said first cuff means together about the axis which extends along the upper portion of the arm of the patient.

13. An apparatus as set forth in claim 1 wherein said drive means includes a manually engageable member which is rotatable under the influence of force applied to said manually engageable member by the patient to rotate said first cuff means about the axis which extends along the upper portion of the arm of the patient.

14. An apparatus as set forth in claim 1 further including third cuff means for gripping a trunk of the body of the patient, second drive means connected with said second and third cuff means and disposed beneath an axilla between the trunk and arm of the patient, said second drive means being operable to move said second cuff means relative to said third cuff means.

15. An apparatus as set forth in claim 1 further including support means which rotatably supports said drive member for rotation about the axis which extends along the upper portion of the arm of the patient, said support means being offset to one side of the axis which extends along the upper portion of the arm of the patient.

16. An apparatus for use in effecting relative movement between bones in a body of a patient, said apparatus comprising first cuff means for gripping a lower portion of an arm of the patient, second cuff means for gripping an upper portion of the arm of the patient, drive means connected with said first and second cuff means for rotating said first cuff means about an axis which extends along the upper portion of the arm of the patient, a base member connected with said second cuff means, said drive means includes a drive member movable along an arcuate path relative to said base member, an arcuate guide surface connected with one of said base and drive members, and a follower connected with a second one of said base and drive members and disposed in engagement with said arcuate guide surface, said arcuate guide surface having a center of curvature which is disposed on the axis which extends along the upper portion of the arm of the patient, said follower and guide surface cooperating to guide movement of said drive member along the arcuate path.

17. An apparatus as set forth in claim 16 wherein said drive means further includes an arcuate array of teeth disposed on said drive member and having a center of curvature which is disposed on the axis which extends along the upper portion of the arm of the patient.

18. An apparatus as set forth in claim 16 wherein said drive means further includes a second arcuate array of teeth disposed in meshing engagement with said arcuate array of teeth on said drive member, said second arcuate array of teeth being rotatable relative to said base member about an axis which extends along the upper portion of the arm of the patient to effect movement of said drive member relative to said base member along the arcuate path.

19. An apparatus as set forth in claim 16 wherein said drive member at least partially defines an opening through which a portion of the arm of the patient extends.

20. An apparatus for use in effecting relative movement between bones in a body of a patient, said apparatus comprising first cuff means for gripping a lower portion of an arm of the patient, second cuff means for gripping an upper portion of the arm of the patient, and drive means connected with said first and second cuff means for rotating said first cuff means about an axis which extends along the upper portion of the arm of the patient, said drive means includes a gear having gear teeth disposed in an arcuate array which forms only a portion of a circle and has spaced apart end portions, said gear having an opening which extends through a peripheral portion of said gear and between spaced apart end portions of said arcuate array of gear teeth, said first cuff means being connected to said gear and being rotatable with said gear, said second cuff means being aligned with the opening in said gear to enable a portion of the arm of the patient to be disposed in the opening in said gear when the lower portion of the arm of the patient is gripped by said first cuff means and the upper portion of the arm of the patient is gripped by said second cuff means.

21. An apparatus as set forth in claim 1 wherein the axis which extends along the upper portion of the arm of the patient extends through the opening in said gear and said drive means is operable to rotate said gear and said first cuff means together about the axis which extends along the upper portion of the arm of the patient.

22. An apparatus as set forth in claim 1 wherein said drive means includes a manually engageable member which is rotatable under the influence of force applied to said manually engageable member by the patient to rotate said first cuff means about the axis which extends along the upper portion of the arm of the patient.

23. An apparatus as set forth in claim 1 further including third cuff means for gripping a trunk of the body of the patient, second drive means connected with said second and third cuff means and disposed beneath an axilla between the trunk and arm of the patient, said second drive means being operable to move said second cuff means relative to said third cuff means.

24. An apparatus for use in effecting relative movement between bones in a body of a patient, said apparatus comprising a first cuff arm, a first cuff which is connected with said first cuff arm and grips a lower portion of an arm of the patient, a second cuff arm connected with said first cuff arm, a second cuff which is connected with said second cuff arm and grips an upper portion of the arm of the patient, and a drive assembly connected with said first and second cuff arms and operable to rotate said first cuff arm and said first cuff relative to said second cuff arm and said second cuff about an axis which extends along said second cuff arm and through said second cuff, said drive assembly includes a main gear which is fixedly connected with said first cuff arm and a second gear which is rotatably mounted on said second cuff arm and is disposed in meshing engagement with said main gear.

25. An apparatus as set forth in claim 24 wherein said first cuff arm has a longitudinal central axis which extends perpendicular to a longitudinal central axis of said second cuff arm during rotation of said first cuff arm and said first cuff relative to said second cuff arm and said second cuff by said drive assembly.

26. An apparatus as set forth in claim 24 wherein said main gear is rotatable about an axis extending parallel to a longitudinal central axis of said second cuff arm.

27. An apparatus as set forth in claim 24 further including a third cuff arm connected with said second cuff arm, a third cuff which is connected with said third cuff arm and grips a trunk of a body of the patient, and a secondary drive assembly connected with said second and third cuff arms and operable to rotate said second cuff arm relative to said third cuff arm about an axis which extends transverse to the axis which extends along said second cuff arm and through said second cuff.

28. An apparatus as set forth in claim 24 wherein said second gear is rotatable relative to said second cuff arm to rotate said first gear and said first cuff arm about the axis which extends along said second cuff arm and through said second cuff, an arcuate track being connected with a first one of said main gear and said second cuff arm, and a follower connected with a second one of said main gear and said second cuff arm and engaging said arcuate track to guide relative movement between said main gear and said second cuff arm.

29. An apparatus as set forth in claim 24 wherein said main gear has an opening which receives at least a portion of the patient's arm during rotation of said first cuff arm and said first cuff relative to said second cuff arm and second cuff.

30. An apparatus as set forth in claim 24 wherein said drive assembly is operable to rotate said first cuff about the axis which extends along the second cuff arm and through said second cuff with an elbow between the upper and lower portions of the arm of the patient bent.

31. An apparatus as set forth in claim 24 further including a third cuff arm connected with said second cuff arm, and third cuff connected with said third cuff arm and a trunk of the patient's body.

32. An apparatus as set forth in claim 31 further including a second drive assembly connected with said second and third cuff arms for rotating said first and second cuff arms together relative to said third cuff arm about an axis which extends transverse to the axis which extends along said second cuff arm.

33. An apparatus as set forth in claim 24 further including a second drive assembly connected with said first and second cuffs for rotating said first and second cuffs together about an axis which extends transverse to the axis which extends along the upper portion of the arm of the patient.

34. Apparatus as set forth in claim 24 wherein said main gear at least partially defines an opening and a portion of the arm of the patient located between said first and second cuffs is disposed in the opening in said main gear.

35. An apparatus as set forth in claim 24 wherein said main gear is movable along an arcuate path relative to said second cuff arm, an arcuate guide surface connected with one of said second cuff arm and main gear, a follower connected with a second one of said second cuff arm and main gear and disposed in engagement with said arcuate guide surface, said arcuate guide surface having a center of curvature which is disposed on the axis which extends along said second cuff arm, said follower and guide surface cooperating to guide movement of said main gear along the arcuate path.

36. An apparatus as set forth in claim 24 wherein said main gear has gear teeth disposed in an arcuate array which forms only a portion of a circle and has spaced apart end portions, said main gear having an opening which extends through a peripheral portion of said main gear and between spaced apart end portions of said arcuate array of gear teeth, said first cuff being connected to said main gear and being rotatable with said main gear, said second cuff being aligned with the opening in said main gear to enable a portion of the arm of the patient to be disposed in the opening in said main gear when the lower portion of the arm of the patient is gripped by said first cuff and the upper portion of the arm of the patient is gripped by said second cuff.

37. An apparatus as set forth in claim 36 wherein the axis which extends along the second cuff arm and through said second cuff also extends through the opening in said main gear and said drive assembly is operable to rotate said main gear and said first cuff together about the axis which extends along said second cuff arm and through said second cuff.

38. An apparatus as set forth in claim 24 wherein said drive assembly includes a manually engageable member which is rotatable under the influence of force applied to said manually engageable member by the patient to rotate said first cuff about the axis which extends along said second cuff arm and through said second cuff.

39. An apparatus as set forth in claim 24 further including third cuff which grips a trunk of the body of the patient, a second drive assembly connected with said second and third cuff and disposed beneath an axilla between the trunk and arm of the patient, said second drive assembly being operable to move said second cuff relative to said third cuff.

40. An apparatus as set forth in claim 24 wherein the axis which extends along said second cuff arm and through said second cuff also extends through said main gear.

41. An apparatus as set forth in claim 40 wherein said second gear is rotatable about an axis which extends parallel to and is offset from the axis which extends along said second cuff arm and through said second cuff.

42. An apparatus as set forth in claim 24 wherein said drive assembly further includes a retainer which is connected with said second cuff arm and engages said main gear to position said main gear relative to said second cuff arm.

43. An apparatus as set forth in claim 24 wherein said main gear is rotatable about the axis which extends along said second cuff arm and through said second cuff.

44. An apparatus for use in effecting relative movement between bones in a body of a patient, said apparatus comprising a first cuff arm, a first cuff which is connected with said first cuff arm and grips a lower portion of an arm of the patient, a second cuff arm connected with said first cuff arm, a second cuff which is connected with said second cuff arm and grips an upper portion of the arm of the patient, and a drive assembly connected with said first and second cuff arms and operable to rotate said first cuff arm and said first cuff relative to said second cuff arm and said second cuff about an axis which extends along said second cuff arm and through said second cuff, said drive assembly includes a first gear connected with said first cuff arm and rotatable relative to said second cuff arm, a second gear connected with said second cuff arm and disposed in meshing engagement with said first gear, said second gear being rotatable relative to said second cuff arm to rotate said first gear and said first cuff arm about the axis which extends along said second cuff arm and through said second cuff, an arcuate track connected with a first one of said first gear and said second cuff arm, and a follower connected with a second one of said first gear and said second cuff arm and engaging said arcuate track to guide relative movement between said first gear and said second cuff arm.

45. An apparatus as set forth in claim 44 wherein the axis which extends along said second cuff arm and through said second cuff extends through said first gear.

46. An apparatus as set forth in claim 44 wherein said first and second gears are rotatable about axes which extend parallel to the axis which extends along said second cuff arm and through said second cuff.

47. An apparatus as set forth in claim 44 wherein said first gear at least partially defines an opening through which a portion of the arm of the patient extends.

48. An for use in effecting relative movement between bones in a body of a patient, said apparatus comprising a first cuff arm, first cuff which is connected with said first cuff arm and grips a lower portion of an arm of the patient, a second cuff arm connected with said first cuff arm, a second cuff which is connected with said second cuff arm and grips an upper portion of the arm of the patient, and a drive assembly connected with said first and second cuff arms and operable to rotate said first cuff arm and said first cuff relative to said second cuff arm and said second cuff about an axis which extends along said second cuff arm and through said second cuff, said drive assembly includes a gear which is rotatable about the axis which extends along the second cuff arm and through the second cuff, said gear has an arcuate array of gear teeth which form a portion of a circle, said gear having an opening which extends through a central portion of said gear and which receives at least a portion of the patient's arm during rotation of said first cuff arm and said first cuff relative to said second cuff arm and second cuff.

49. An apparatus as set forth in claim 48 wherein said drive assembly includes a second gear which is disposed in meshing engagement with said gear which is rotatable about the axis which extends along the second cuff arm and through the second cuff, and a manually engagable member which is connected with said second gear and is rotatable under the influence of force applied to said manually engagable member to rotate said second gear.

50. An apparatus as set forth in claim 48 further including a third cuff which grips a trunk of the body of the patient, a second drive assembly connected with said second and third cuff and disposed beneath an axilla between the trunk and arm of the patient, said second drive assembly being operable to move said second cuff relative to said third cuff.

51. An apparatus as set forth in claim 48 wherein said first cuff arm has a longitudinal central axis which extends perpendicular to a longitudinal central axis of said second cuff arm during rotation of said first cuff arm and said first cuff relative to said second cuff arm and said second cuff by said drive assembly.

52. An apparatus as set forth in claim 48 wherein said gear is mounted on said second cuff arm, said first cuff arm being connected with said gear for rotation therewith relative to said second cuff arm.

53. An apparatus for use in effecting relative movement between bones in a body of a patient, said apparatus comprising a first cuff arm, a first cuff connected with said first cuff arm to hold a lower portion of an arm of a patient, a second cuff arm, a second cuff connected with said second cuff arm to hold an upper portion of the arm of the patient, and a gear rotatably mounted on said second cuff arm and rotatable about an axis which extends along said second cuff arm, said first cuff arm being connected with said gear for rotation therewith and extending outward from said gear in a direction transverse to the axis of rotation of said gear, said gear includes surface means which defines an opening which extends through said gear and receives a portion of the arm of the patient disposed between said first and second cuffs.

54. An apparatus as set forth in claim 53 wherein said first cuff arm has longitudinal central axis which extends perpendicular to a longitudinal central axis of said second cuff arm.

55. An apparatus as set forth in claim 53 wherein said first cuff arm is fixedly connected with said gear and is spaced from said second cuff arm.

56. An apparatus as set forth in claim 53 further including a second gear mounted on said second cuff arm in meshing engagement with said gear, said second gear being rotatable about an axis which extends transverse to the axis about which said gear is rotatable.

57. An apparatus for use in effecting relative movement between bones in a body of a patient, said apparatus comprising a first member, means for connecting said first member with a lower portion of an arm of the patient, a second member connected with said first member, means for connecting said second member with an upper portion of an arm of a patient, a third member, connector means for pivotally interconnecting said second and third members, means for connecting said third member with a trunk of the body of the patient with said connector means which pivotally interconnects said second and third members disposed beneath an axilla between the arm and trunk of the patient, first drive means for rotating said first member and the lower portion of the arm of the patient relative to the second member about an axis which extends along the upper portion of the arm of the patient, and second drive means which is at least partially disposed beneath the axilla between the arm and trunk of the patient for moving said first and second members relative to said third member about an axis extending through said connector means.

58. An apparatus as set forth in claim 57 wherein said first drive means includes a gear which is rotatable relative to said second member about the axis which extends along the upper portion of the arm of the patient, said first member being connected with said gear for rotation therewith relative to said second member.

59. An apparatus as set forth in claim 58 wherein said gear includes surface means for at least partially defining an opening through which a portion of the arm of the patient extends.

60. An apparatus as set forth in claim 59 wherein said first drive means includes a worm which is rotatably mounted on said second member and is drivingly connected with said gear.

61. An apparatus as set forth in claim 57 wherein said first drive means includes a first gear having an opening which receives a portion of the arm of the patient, said first member extends into the opening in said gear and is fixedly connected with said gear, and a second gear rotatably mounted on said first member and disposed in meshing engagement with said first gear, said second gear being rotatable relative to said second member to rotate said first gear and said first member relative to said second member.

62. An apparatus as set forth in claim 57 wherein said second drive means includes a drive member which is rotatable about an axis extending through said connector means and a driven member is movable toward and away from said connector means by said drive member to effect movement of said first and second member relative to said third member.

63. An apparatus for use in effecting relative movement between bones in a body of a patient, said apparatus comprising a first member, means for connecting said first member with a lower portion of an arm of the patient, a second member connected with said first member, means for connecting said second member with an upper portion of an arm of a patient, a third member, connector means for pivotally interconnecting said second and third members, means for connecting said third member with a trunk of the body of the patient with said connector means which pivotally interconnects said second and third members disposed beneath an axilla between the arm and trunk of the patient, and drive means for rotating said first member and the lower portion of the arm of the patient relative to the second member about an axis which extends along the upper portion of the arm of the patient, said drive means includes a gear which is rotatable relative to said second member about the axis which extends along the upper portion of the arm of the patient, said first member being connected with said gear for rotation therewith relative to said second member, said gear includes surface means for at least partially defining an opening through which a portion of the arm of the patient extends, said drive means includes a worm which is rotatably mounted on said second member and is drivingly connected with said gear.

64. An apparatus for use in effecting relative movement between bones in a body of a patient, said apparatus comprising a first member, means for connecting said first member with a lower portion of an arm of the patient, a second member connected with said first member, means for connecting said second member with an upper portion of an arm of a patient, a third member, connector means for pivotally interconnecting said second and third members, means for connecting said third member with a trunk of the body of the patient with said connector means which pivotally interconnects said second and third members disposed beneath an axilla between the arm and trunk of the patient, and drive means for rotating said first member and the lower portion of the arm of the patient relative to the second member about an axis which extends along the upper portion of the arm of the patient, said drive means includes a first gear having an opening which receives a portion of the arm of the patient, said first member extends into the opening in said gear and is fixedly connected with said gear, and a second gear rotatably mounted on said first member and disposed in meshing engagement with said first gear, said second gear being rotatable relative to said second member to rotate said first gear and said first member relative to said second member.

65. An apparatus as set forth in claim 64 further including second drive means which is at least partially disposed beneath the axilla between the arm and trunk of the patient for moving said first and second members relative to said third member about an axis extending through said connector means.

66. An apparatus for use in effecting relative movement between bones in a body of a patient, said apparatus comprising a first cuff which is engageable with a lower portion of an arm of the patient, a second cuff which is engageable with an upper portion of the arm of the patient and which is connected with said first cuff, said second cuff having a central axis which extends transverse to a central axis of said first cuff, a third cuff which is engageable with a trunk portion of the body of the patient and which is connected with said second cuff, a main drive assembly connected with said first and second cuffs and operable to rotate said first cuff about an axis extending through said second cuff, and a second drive assembly connected with said second and third cuffs and operable to rotate said first and second cuffs together about an axis which extends through a connection between said second and third cuffs, said main drive assembly includes a drive member which is connected with said first cuff and is rotatable about the central axis of said second cuff with said first cuff, said drive member at least partially defines an opening and a portion of the arm of the patient is received in the opening in said drive member.

67. An apparatus as set forth in claim 66 wherein the central axis of said first cuff extends perpendicular to and intersects the central axis of said second cuff.

68. An apparatus as set forth in claim 66 wherein operation of said second drive assembly is effective to rotate said main drive assembly with said first and second cuffs about the axis which extends through the connection between said second and third cuffs.

69. An apparatus as set forth in claim 66 further including a fourth cuff which is connected with said first and second cuffs and is engageable with an elbow disposed between the upper and lower portions of the arm of the patient.

70. An apparatus as set forth in claim 66 further including a fourth cuff which is connected with said third cuff and is engageable with a hand of the patient which is connected with the lower portion of the arm of the patient.

71. An apparatus as set forth in claim 70 wherein said fourth cuff includes an arcuate surface which is engageable with a palm portion of the hand of the patient and a strap which is engageable with a back portion of the hand of the patient.

72. An apparatus as set forth in claim 66 wherein said second drive assembly is at least partially disposed between said second and third cuffs.

73. An apparatus as set forth in claim 66 wherein the connection between said second and third cuffs is disposed beneath an axilla between the upper portion of the patient and the trunk of the patient when said third cuff is connected with the trunk of the patient.

74. An apparatus for use in effecting relative movement between bones in a body of a patient, said apparatus comprising a first cuff arm, a hand cuff which is connected with said first cuff arm and grips a hand connected with an arm of the patient, said hand cuff including an arcuate surface which is engaged by a palm on the hand of the patient, a lower cuff which is connected with said first cuff arm and holds a lower portion of the arm of the patient in a position in which a longitudinal central axis of the lower portion of the arm of the patient intersects said arcuate surface of said hand cuff, a second cuff arm connected with said first cuff arm, an upper cuff which is connected with said second cuff arm and holds an upper portion of the arm of the patient, and a drive assembly connected with said first cuff arm and operable to rotate said first cuff arm about an axis which extends transverse to the longitudinal central axis of the lower portion of the arm of the patient while the arm of the patient is held by said upper and lower cuffs and the hand of the patient is held by said hand cuff with the palm on the hand of the patient in engagement with said arcuate surface, said drive assembly includes a main gear which is fixedly connected with said first cuff arm, and a second gear which is disposed in meshing engagement with said main gear, said second gear being rotatable under the influence of force transmitted from the patient to effect rotation of said main gear, first cuff arm, lower cuff, and hand cuff about the axis which extends transverse to the lower portion of the arm of the patient.

75. An apparatus as set forth in claim 74 wherein said lower cuff has a longitudinal central axis which extends perpendicular to a longitudinal central axis of said upper cuff.

76. An apparatus as set forth in claim 74 further including a third cuff arm which is pivotally connected with said second cuff arm, a base cuff which is connected with said third cuff arm and grips a trunk of the patient, and a second drive assembly which is connected with said second and third cuff arms and is operable to effect pivotal movement between said second and third cuff arms.

77. An apparatus for use in effecting relative movement between bones in a body of a patient, said apparatus comprising first means for holding an upper portion of an arm of the patient against sidewise movement in a direction transverse to a longitudinal central axis of the upper portion of the arm of the patient, and second means connected with said first means for applying force to a lower portion of the arm of the patient to rotate a bone in the upper portion of the arm of the patient about a central axis of the upper portion of the arm of the patient while said first means holds the upper portion of the arm of the patient against sidewise movement in a direction transverse to the longitudinal central axis of the upper portion of the arm of the patient, said second means includes a first gear which is connected with the lower portion of the arm of the patient, a second gear which is disposed in meshing engagement with said first gear, and a manually rotatable input member which is connected with said second gear and is manually rotatable to effect rotation of said first and second gears.

78. An apparatus as set forth in claim 77 wherein said second means holds the arm of the patient with a bend in the arm of the patient at an elbow between the upper and lower portions of the arm of the patient.

79. An apparatus as set forth in claim 77 wherein said first means includes first cuff means for gripping the upper portion of the arm of the patient, second cuff means for gripping a trunk portion of the body of the patient, and means for holding said first and second cuff means against movement relative to each other.

80. An apparatus as set forth in claim 77 wherein said first gear is rotatable with the lower portion of the arm of the patient about an axis which extends parallel to the central axis of the upper portion of the arm of the patient.

81. An apparatus as set forth in claim 77 wherein said first gear at least partially defines an opening through which a portion of the arm of the patient extends.

82. An apparatus as set forth in claim 77 wherein said first and second gears are rotatable about parallel axes which extend parallel to the central axis of the upper portion of the arm of the patient.

83. An apparatus for use in effecting relative movement between bones in a body of a patient, said apparatus comprising a first cuff arm, a first cuff which is connected with said first cuff arm and grips a lower portion of an arm of the patient, a second cuff arm connected with said first cuff arm, a second cuff which is connected with said second cuff arm and grips an upper portion of the arm of the patient, and a drive assembly connected with said first and second cuff arms, said drive assembly includes an input member which is manually rotatable to effect rotation of said first cuff arm and said first cuff relative to said second cuff arm and said second cuff about an axis which extends along said second cuff arm under the influence of force transmitted from said input member to said first cuff arm by said drive assembly.

84. An apparatus as set forth in claim 83 wherein said first cuff arm has a longitudinal central axis which extends perpendicular to a longitudinal central axis of said second cuff arm during rotation of said first cuff arm and said first cuff relative to said second cuff arm and said second cuff under the influence of force transmitted from said input member by said drive assembly.

85. An apparatus as set forth in claim 83 wherein said drive assembly includes a gear mounted on said second cuff arm and rotatable about an axis which extends along said second cuff arm, said first cuff arm being connected with said gear for rotation therewith relative to said second cuff arm.

86. An apparatus as set forth in claim 83 further including a third cuff arm connected with said second cuff arm, a third cuff which is connected with said third cuff arm and grips a trunk of a body of the patient, and a secondary drive assembly connected with said second and third cuff arms, said secondary drive assembly includes a second input member which is manually rotatable to effect rotation of said second cuff arm relative to said third cuff arm about an axis which extends transverse to the axis which extends along said second cuff arm under the influence of force transmitted from said second input member to said second cuff arm by said secondary drive assembly.

87. An apparatus as set forth in claim 83 wherein said drive assembly includes a first gear which is fixedly connected with said first cuff arm and a second gear which is rotatably mounted on said second cuff arm and is disposed in meshing engagement with said first gear, said input member being manually rotatable to effect rotation of said first and second gears.

88. An apparatus as set forth in claim 87 wherein said drive assembly further includes a retainer which is connected with said second cuff arm and engages said first gear to position said first gear relative to said second cuff arm.

89. An apparatus as set forth in claim 87 wherein said first gear is rotatable about the axis which extends along said second cuff arm.

90. An apparatus as set forth in claim 83 wherein said drive assembly includes a first gear connected with said first cuff arm and rotatable relative to said second cuff arm, a second gear connected with said second cuff arm and said input member, second gear being disposed in meshing engagement with said first gear, said second gear being rotatable relative to said second cuff arm under the influence of force transmitted from said input member to said second gear to rotate said first gear and said first cuff arm about the axis which extends along said second cuff arm, an arcuate track connected with a first one of said first gear and said second cuff arm, and a follower connected with a second one of said first gear and said second cuff arm and engaging said arcuate track to guide relative movement between said first gear and said second cuff arm.

91. An apparatus as set forth in claim 83 wherein said drive assembly includes a gear which is rotatable about the axis which extends along the second cuff arm, said gear has an arcuate array of gear teeth which form a portion of a circle, said gear having an opening which extends through a central portion of said gear and which receives at least a portion of the patient's arm during rotation of said first cuff arm and said first cuff relative to said second cuff arm and second cuff.

92. An apparatus for use in effecting relative movement between bones in a body of a patient, said apparatus comprising a first cuff which grips a lower portion of an arm of the patient, a second cuff which grips an upper portion of the arm of the patient, and a drive assembly connected with said first and second cuffs, said drive assembly includes an input member which is rotatable to effect rotation of said first cuff about an axis which extends along the upper portion of the arm of the patient and through the second cuff under influence of force transmitted from said input member through said drive assembly to said first cuff.

93. An apparatus as set forth in claim 92 wherein said drive assembly is operable to rotate said first cuff about the axis which extends along the upper portion of the arm of the patient and through the second cuff with an elbow between the upper and lower portions of the arm of the patient bent.

94. An apparatus as set forth in claim 92 further including a first cuff arm connected with said first cuff and a second cuff arm connected with said second cuff, said drive assembly being operable under the influence of force transmitted from said input member to rotate said first cuff arm and said first cuff together relative to said second cuff arm about the axis which extends along the upper portion of the arm of the patient and through the second cuff.

95. An apparatus as set forth in claim 94 further including a third cuff arm connected with said second cuff arm, and a third cuff which connects said third cuff arm with a trunk of the patient's body.

96. An apparatus as set forth in claim 95 further including a second drive assembly connected with said second and third cuff arms, said second drive assembly includes a second input member which is rotatable to effect rotation of said first and second cuff arms together relative to said third cuff arm about an axis which extends transverse to the axis which extends along the upper portion of the arm of the patient under the influence of force transmitted from said second input member through said second drive assembly to said second cuff arm.

97. An apparatus as set forth in claim 92 further including a second drive assembly connected with said first and second cuffs, said second drive assembly being operable to transmit force which effects rotation of said first and second cuffs together about an axis which extends transverse to the axis which extends along the upper portion of the arm of the patient and through the second cuff.

98. An apparatus as set forth in claim 92 wherein said drive assembly includes a drive member which is rotatable about the axis which extends along the upper portion of the arm of the patient and through the second cuff, said first cuff being connected with said drive member for rotation therewith.

99. An apparatus as set forth in claim 98 wherein said drive member at least partially defines an opening and a portion of the arm of the patient located between said first and second cuffs is disposed in the opening.

100. An apparatus as set forth in claim 99 further including a support assembly which rotatably supports said drive member for rotation about the axis which extends along the upper portion of the arm of the patient and through said second cuff, said support assembly being offset to one side of the axis which extends along the upper portion of the arm of the patient and through the second cuff.

101. An apparatus as set forth in claim 92 further including a base member connected with said second cuff means, said drive assembly includes a drive member movable along an arcuate path relative to said base member, an arcuate guide surface connected with one of said base and drive members, a follower connected with a second one of said base and drive members and disposed in engagement with said arcuate guide surface, said follower and guide surface cooperating to guide movement of said drive member along the arcuate path.

102. An apparatus as set forth in claim 92 further including a first cuff arm connected with said first cuff, and a second cuff arm connected with said second cuff, said first and second cuff arms being interconnected by said drive assembly, said input member being rotatably mounted on said second cuff arm.

103. An apparatus as set forth in claim 102 further including a third cuff arm pivotally connected with said second cuff arm and a third cuff which connects said third cuff arm with a trunk of the patient's body.

104. An apparatus as set forth in claim 92 wherein said drive assembly includes a drive member which is rotatable about the axis which extends along the upper portion of the arm of the patient and through said second cuff under the influence of force transmitted from said input member to said drive member, said first cuff arm being fixedly connected with said drive member and being rotatable with said drive member about the axis which extends along the upper portion of the arm of the patient and through said second cuff.

105. An apparatus as set forth in claim 92 wherein said drive assembly includes a gear having teeth disposed in an arcuate array which forms only a portion of a circle and has spaced apart end portions, said gear having an opening which extends through a peripheral portion of said gear and between spaced apart end portions of said arcuate array of teeth, said first cuff being connected to said gear and being rotatable with said gear, said second cuff being aligned with the opening in said gear to enable a portion of the arm of the patient to be disposed in the opening in said gear when the lower portion of the arm of the patient is gripped by said first cuff and the upper portion of the arm of the patient is gripped by said second cuff.

106. An apparatus as set forth in claim 105 wherein the axis which extends along the upper portion of the arm of the patient and through said second cuff also extends through the opening in said gear, said drive assembly is operable to rotate said gear and said first cuff together about the axis which extends along the upper portion of the arm of the patient and through said second cuff under the influence of force transmitted from said input member.

107. An apparatus as set forth in claim 92 wherein said input member is rotatable under the influence of force applied to said input member by the patient to rotate said first cuff about the axis which extends along the upper portion of the arm of the patient and through said second cuff.

108. An apparatus as set forth in claim 92 further including a third cuff which grips a trunk of the body of the patient, a second drive assembly connected with said second and third cuffs and disposed beneath an axilla between the trunk and arm of the patient, said second drive assembly being operable to transmit force which moves said second cuff relative to said third cuff.

109. An apparatus for use in effecting relative movement between bones in a body of a patient, said apparatus comprising a first cuff arm, a first cuff connected with said first cuff arm to hold a lower portion of an arm of a patient, a second cuff arm, a second cuff connected with said second cuff arm to hold an upper portion of the arm of the patient, and a gear rotatably mounted on said second cuff arm and rotatable about an axis which extends along said second cuff arm and through said second cuff, said first cuff arm having a first portion connected to said gear for rotation therewith, said first cuff arm having a second portion connected with said first cuff.

110. An apparatus as set forth in claim 109 wherein said first cuff arm has longitudinal central axis which extends through said gear in a direction perpendicular to a longitudinal central axis of said second cuff arm.

111. An apparatus as set forth in claim 109 further including a second gear mounted on said second cuff arm in meshing engagement with said gear, said second gear being rotatable about an axis which extends parallel to the axis about which said gear is rotatable.

112. An apparatus as set forth in claim 109 further including a manually engageable member which is connected with said gear and is rotatable under the influence of force applied to said manually engageable member to rotate said gear and said first cuff arm relative to said second cuff arm.

113. An apparatus as set forth in claim 109 wherein said gear includes surface means which defines an opening which extends through said gear, said first portion of said first cuff arm extends into the opening in said gear.

114. An apparatus for use in effecting relative movement between bones in a body of a patient, said apparatus comprising a first cuff which is engageable with a lower portion of an arm of the patient, a second cuff which is engageable with an upper portion of the arm of the patient and which is connected with said first cuff, said second cuff having a central axis which extends transverse to a central axis of said first cuff, a third cuff which is engageable with a trunk portion of the body of the patient and which is connected with said second cuff, a main drive assembly connected with said first and second cuffs and operable to transmit force which rotates said first cuff about an axis extending through said second cuff and through said main drive assembly, and a second drive assembly connected with said second and third cuffs and operable to rotate said first and second cuffs together about an axis which extends through a connection between said second and third cuffs.

115. An apparatus as set forth in claim 114 wherein the central axis of said first cuff extends transverse to and intersects the central axis of said second cuff, the central axes of said first and second cuffs both extend through at least a portion of said main drive assembly.

116. An apparatus as set forth in claim 114 wherein operation of said second drive assembly is effective to rotate said main drive assembly with said first and second cuffs about the axis which extends through the connection between said second and third cuffs.

117. An apparatus as set forth in claim 114 further including a fourth cuff which is connected with said first and second cuffs and is engageable with an elbow disposed between the upper and lower portions of the arm of the patient, said fourth cuff having a central axis which extends along a central axis of said first cuff.

118. An apparatus as set forth in claim 114 further including a fourth cuff which is connected with said first cuff and is engageable with a hand of the patient which is connected with the lower portion of the arm of the patient, said fourth cuff having a central axis which extends along a central axis of said first cuff.

119. An apparatus as set forth in claim 118 wherein said fourth cuff includes an arcuate surface which is engageable with a palm portion of the hand of the patient and a strap which is engageable with a back portion of the hand of the patient.

120. An apparatus as set forth in claim 114 wherein said main drive assembly includes a drive member which is connected with said first cuff and is rotatable about the central axis of said second cuff with said first cuff.

121. An apparatus as set forth in claim 114 wherein said drive member at least partially defines an opening and a portion of the arm of the patient is received in the opening in said drive member.

122. An apparatus as set forth in claim 114 wherein said second drive assembly is at least partially disposed between said second and third cuffs.

123. An apparatus as set forth in claim 114 wherein the connection between said second and third cuffs is disposed beneath an axilla between the upper portion of the arm of the patient and the trunk of the patient when said third cuff is connected with the trunk of the patient.

124. An apparatus for use in effecting relative movement between bones in a body of a patient, said apparatus comprising a first cuff arm, a first cuff connected with said first cuff arm to hold a lower portion of an arm of a patient, a second cuff arm, a second cuff connected with said second cuff arm to hold an upper portion of the arm of the patient, and a drive assembly connected with said first and second cuff arms, said drive assembly includes a first gear which is fixedly connected to said first cuff arm and is rotatable about a first axis which extends through said second cuff and a second gear which is disposed in meshing engagement with said first gear, said second gear being rotatable about a second axis to effect rotation of said first gear and said first cuff arm together about said first axis.

125. An apparatus as set forth in claim 124 wherein said first cuff arm has longitudinal central axis which extends transverse to said first axis and extends through a portion of said first gear.

126. An apparatus as set forth in claim 124 further wherein said second gear is rotatably mounted on said second cuff arm, said second gear being rotatable about an axis which extends parallel to the axis about which said first gear is rotatable.

127. An apparatus as set forth in claim 124 further including a manually engageable member which is connected with said second gear and is rotatable under the influence of force applied to said manually engageable member to rotate said first and second gears and said first cuff arm relative to said second cuff arm.

128. An apparatus as set forth in claim 124 wherein said first gear includes an opening which extends through said first gear and receives a portion of the arm of the patient.

129. An apparatus for use in effecting relative movement between bones in a body of a patient, said apparatus comprising a first cuff arm, a first cuff connected with said first cuff arm to hold a lower portion of an arm of a patient, a second cuff arm, a second cuff connected with said second cuff arm to hold an upper portion of an arm of a patient, a first drive assembly connected with said first and second cuff arms and operable to rotate said first cuff arm and said first cuff together relative to said second cuff arm and second cuff, a third cuff arm, a third cuff connected with said third cuff arm to hold a trunk of the patient, and a second drive assembly connected with said first and second cuff arms, said second drive assembly includes an input member which is manually rotatable to effect rotation of said first and second cuff arms and said first and second cuffs relative to said third cuff arm and third cuff under the influence of force transmitted from said input member to said second cuff arm by said second drive assembly.

130. An apparatus as set forth in claim 129 wherein said first and second cuff arms are rotatable together relative to said third cuff arm about a first axis which extends transverse to a longitudinal central axis of said second cuff arm, said input member being rotatable about a second axis which is offset from said first axis to transmit force which effects operation of said second drive assembly to rotate said first and second cuff arms together relative to said third cuff arm.

131. An apparatus as set forth in claim 129 further including a pivot connection interconnecting said first and second cuff arms, said first and second cuff arms have longitudinal axes which extend through said pivot connection, said second drive assembly being operable under the influence of the force transmitted from said input member to rotate said first and second cuff arms together about an axis extending through said pivot connection.

132. An apparatus as set forth in claim 129 wherein said second drive assembly includes an externally threaded member and an internally threaded member disposed in threaded engagement with said externally threaded member, one of said internally and externally threaded members being rotatable relative to the other of said internally and externally threaded members under the influence of force transmitted from said input member to effect rotation of said first and second cuff arms and said first and second cuffs relative to said third cuff arm.

133. An apparatus as set forth in claim 129 wherein said second drive assembly is at least partially disposed beneath an axilla between the upper portion of the arm and the trunk of the patient, said one of said internally and externally threaded members being rotatable about an axis which extends through the axilla between the upper portion of the arm and the trunk of the patient.

134. An apparatus as set forth in claim 129 wherein said input member is manually rotatable about an axis which extends transverse too an axis about which said one of said internally and externally threaded members is rotatable.

* * * * *

UNITED STATES PATENT AND TRADEMARK OFFICE
CERTIFICATE OF CORRECTION

PATENT NO. : 6,113,562
DATED : September 5, 2000
INVENTOR(S) : Peter M. Bonutti, Christopher A. Leo, Kevin R. Ruholl It is certified that error appears in the above-indentified patent and that said Letters Patent is hereby corrected as shown below:

Column 13, line 30, change "3" to "4"

Column 15, line 24, change "1" to "20"

Column 15, line 30, change "1" to "20"

Column 15, line 36, change "1" to "20"

Column 18, line 4, after "AN" insert "apparatus"

Column 28, line 40, change "too" to "to"

Signed and Sealed this

Twenty-ninth Day of May, 2001

Attest:

NICHOLAS P. GODICI

*Attesting Officer*  *Acting Director of the United States Patent and Trademark Office*